United States Patent [19]
Aust et al.

[11] Patent Number: 5,618,294
[45] Date of Patent: Apr. 8, 1997

[54] SURGICAL INSTRUMENT

[75] Inventors: Gilbert M. Aust, Huntsville; Timothy E. Taylor, Hampton Cove, both of Ala.

[73] Assignee: Aust & Taylor Medical Corporation, Huntsville, Ala.

[21] Appl. No.: 505,476

[22] Filed: Jul. 21, 1995

Related U.S. Application Data

[63] Continuation-in-part of Ser. No. 248,507, May 24, 1994, Pat. No. 5,454,827.

[51] Int. Cl.$^6$ ............................................... A61B 17/00
[52] U.S. Cl. ........................... 606/170; 606/174; 606/205; 128/751
[58] Field of Search .............................. 606/51, 52, 108, 606/174, 205–211, 170, 198; 128/3, 4, 6, 751–755

[56] References Cited

U.S. PATENT DOCUMENTS

| | | |
|---|---|---|
| 3,470,876 | 10/1969 | Barchilon . |
| 3,605,725 | 9/1971 | Bentov . |
| 4,499,899 | 2/1985 | Lyons, III . |
| 4,517,977 | 5/1985 | Frost . |
| 4,649,919 | 3/1987 | Thimsen et al. . |
| 4,763,669 | 8/1988 | Jaeger . |
| 4,834,069 | 5/1989 | Umeda . |
| 4,834,729 | 5/1989 | Sjostrom . |
| 4,880,015 | 11/1989 | Nierman . |
| 5,025,804 | 6/1991 | Kondo . |
| 5,143,475 | 9/1992 | Chikama . |
| 5,178,129 | 1/1993 | Chikama et al. . |
| 5,209,747 | 5/1993 | Knoepfler . |
| 5,295,990 | 3/1994 | Levin . |
| 5,330,502 | 7/1994 | Hassler et al. . |
| 5,354,311 | 10/1994 | Kambin et al. . |

FOREIGN PATENT DOCUMENTS

| | | |
|---|---|---|
| 0301288 | 2/1989 | European Pat. Off. . |
| 2662778 | 12/1991 | France . |
| 3920706 | 1/1991 | Germany . |
| 4136861 | 5/1993 | Germany . |
| 4204051 | 8/1993 | Germany . |
| 9300048 | 1/1993 | WIPO . |
| 9304634 | 3/1993 | WIPO . |
| 9320768 | 10/1993 | WIPO . |

OTHER PUBLICATIONS

Raychem Corporation, *Raychem Shape–Memory Alloys*, pp. 1–16, 1989, Advertising Brochure.
A copy of an EPO Search Report dated Jul. 26, 1995.
A copy of an EPO Search Report dated Sep. 1, 1995.

*Primary Examiner*—Michael Powell Buiz
*Assistant Examiner*—William Lewis
*Attorney, Agent, or Firm*—Tarolli, Sündheim, Covell, Tummino & Szabo

[57] ABSTRACT

A surgical instrument includes a handle, a first stem section having a longitudinal axis and extending from the handle, and a tissue engaging member for engaging tissue. A second stem section, connected between the first stem section and the tissue engaging member, has a portion which is bendable and supports the tissue engaging member for movement between a plurality of orientations relative to the axis and to the first stem section. The surgical instrument includes a system for bending the bendable portion of the second stem section to change the orientation of the tissue engaging member relative to the axis and to the first stem section from a first orientation to a second orientation. The bendable portion of the second stem section includes a member for enabling bending movement of the bendable portion to locate the tissue engaging member at the same angle relative to the longitudinal axis of the first stem section at more than one location along the length of the bendable portion.

47 Claims, 12 Drawing Sheets

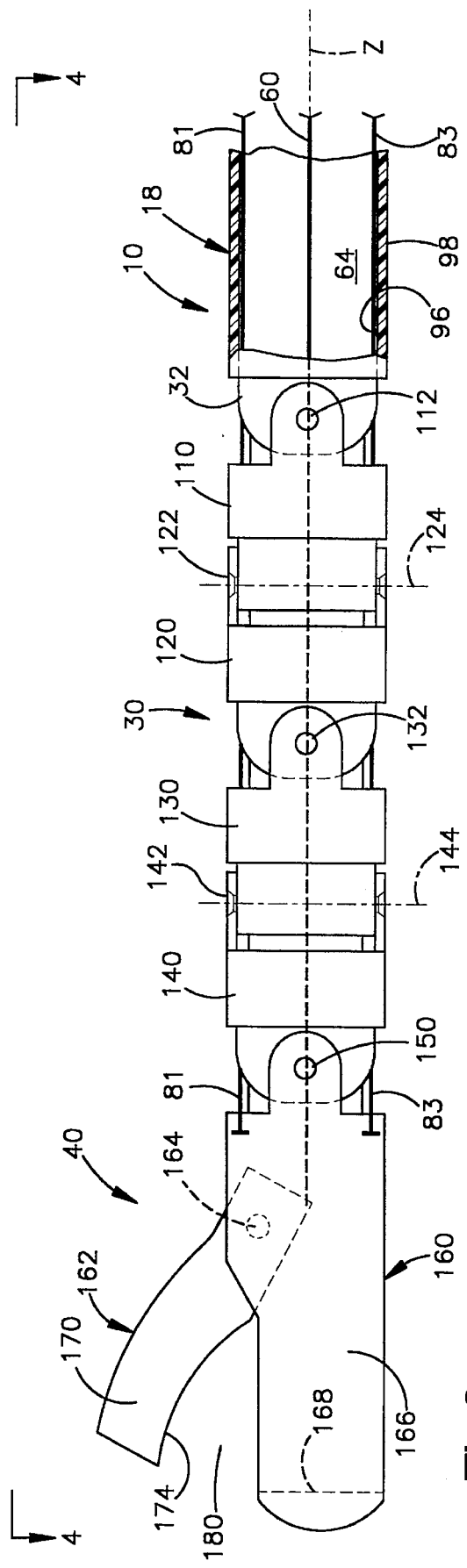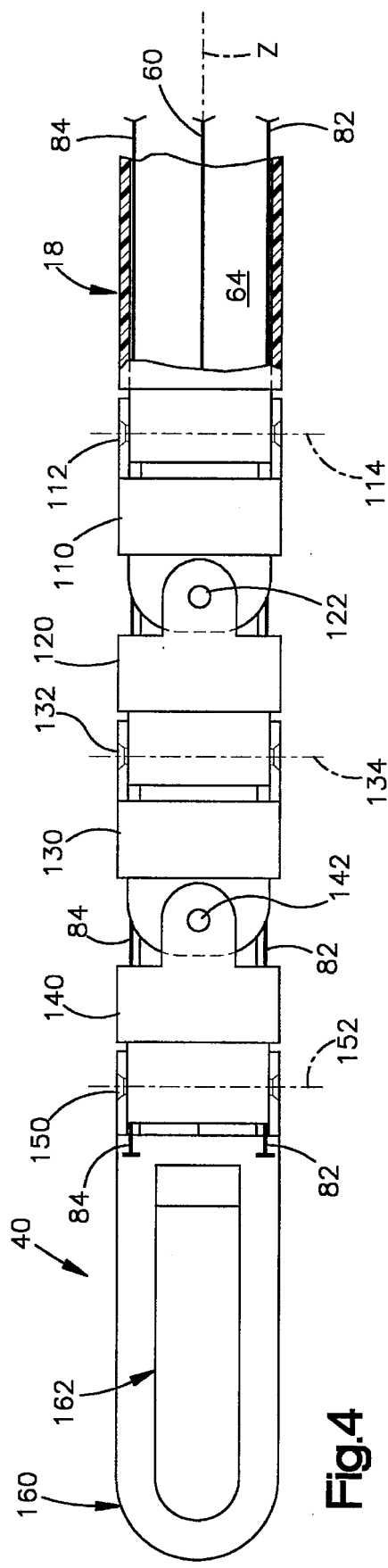

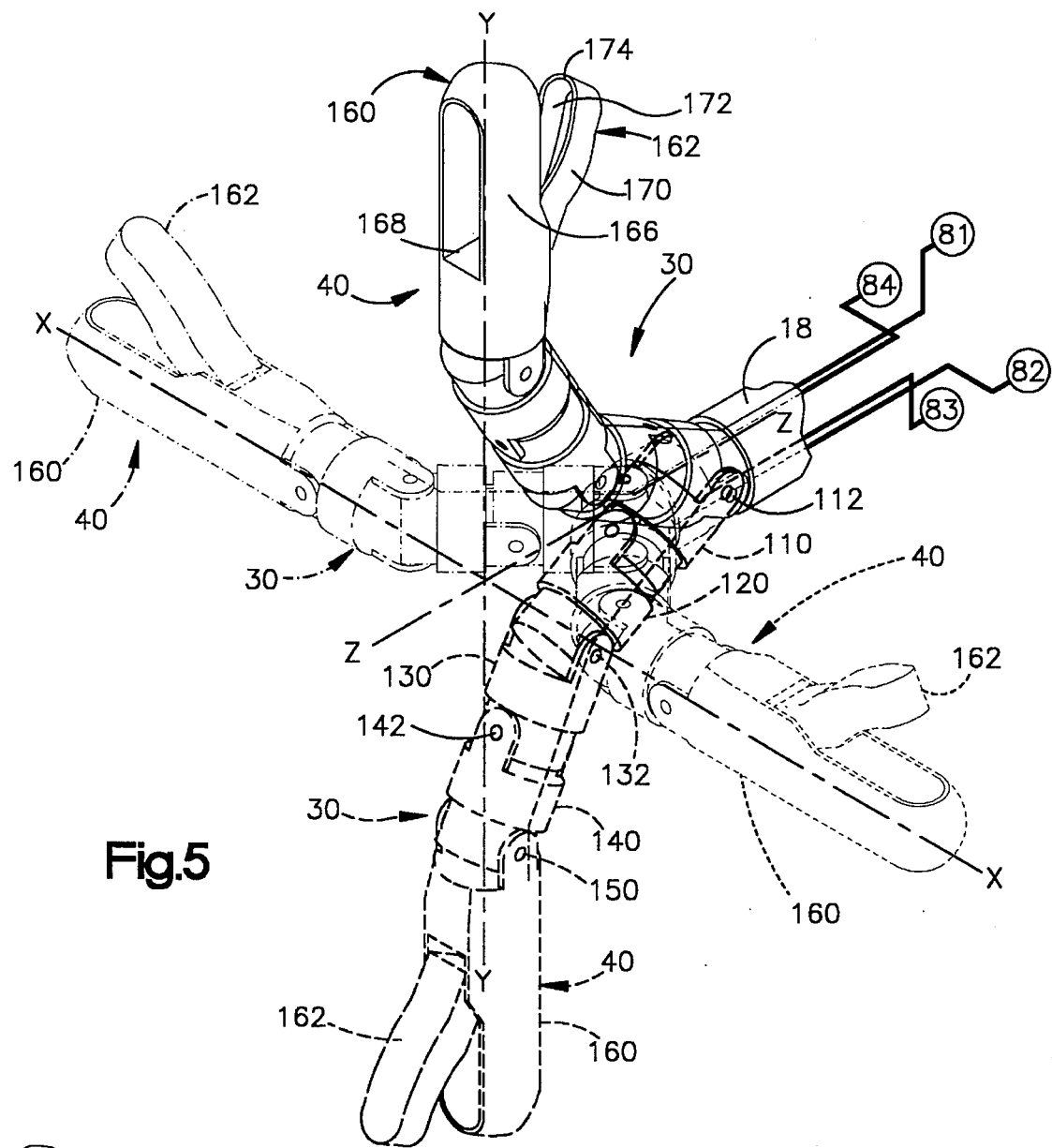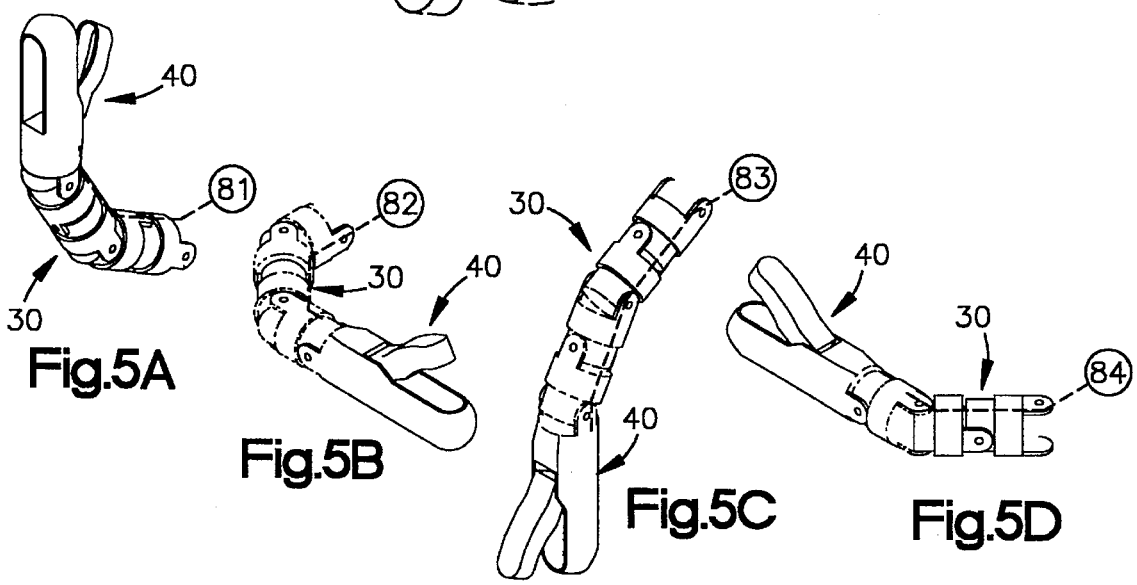

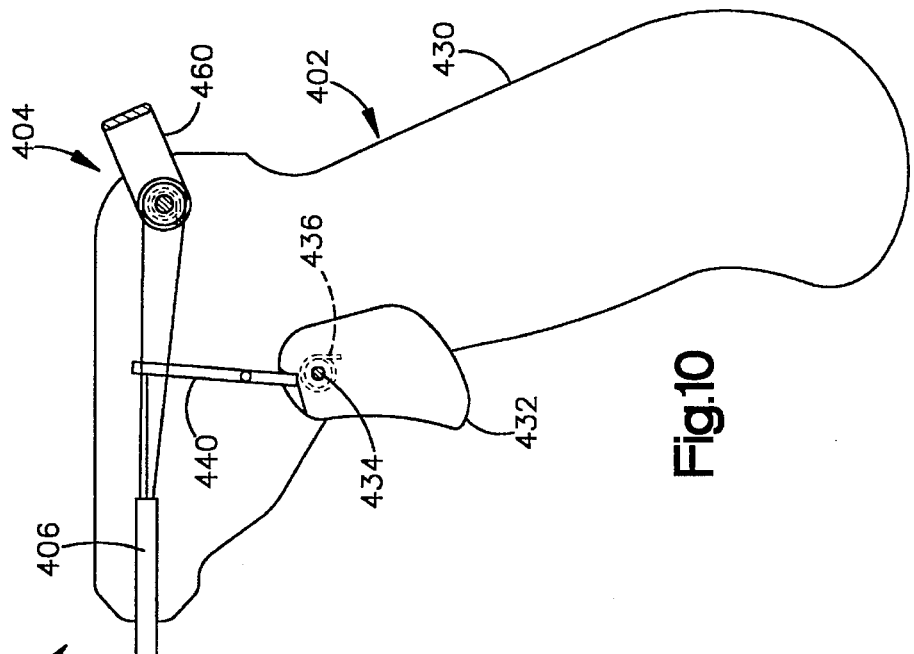
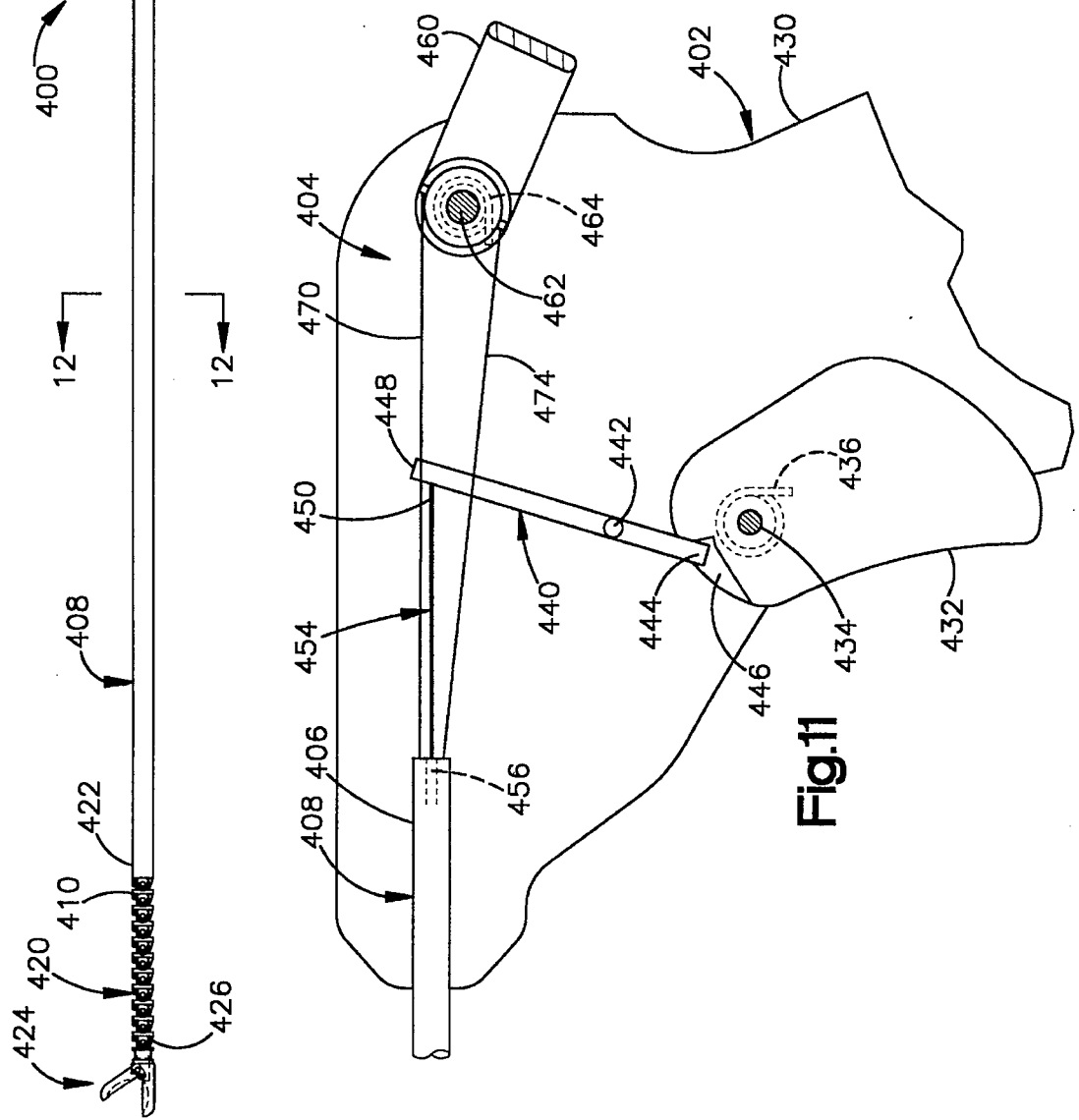

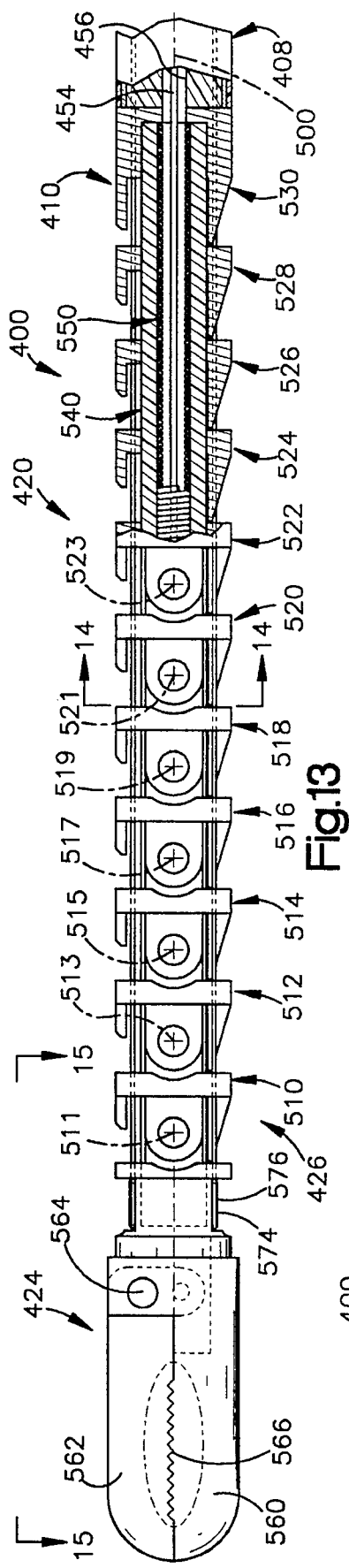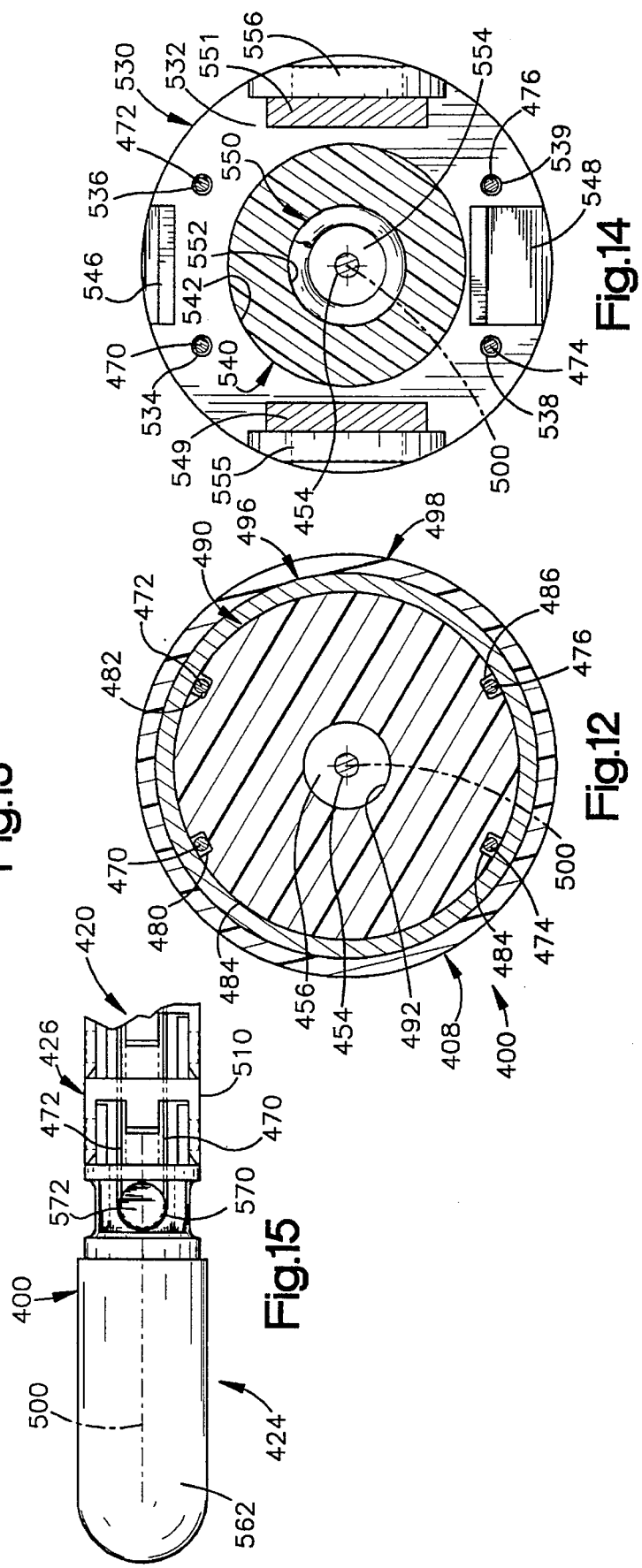

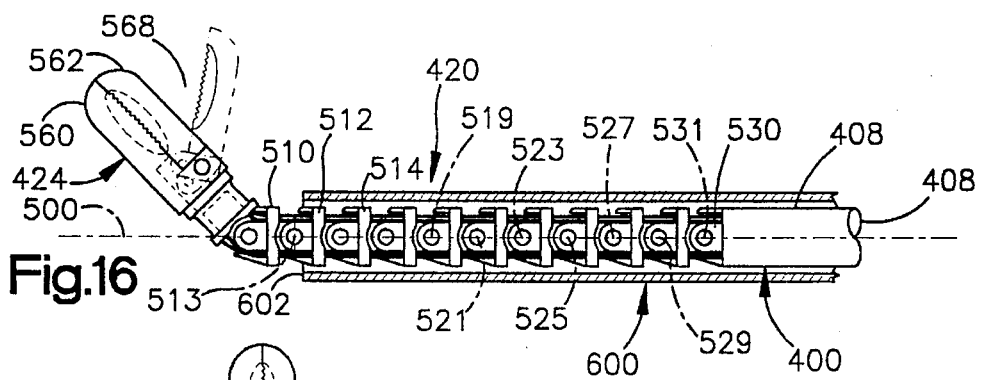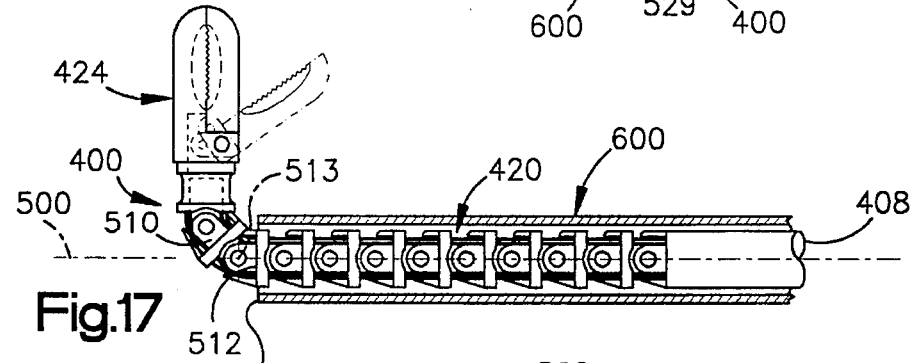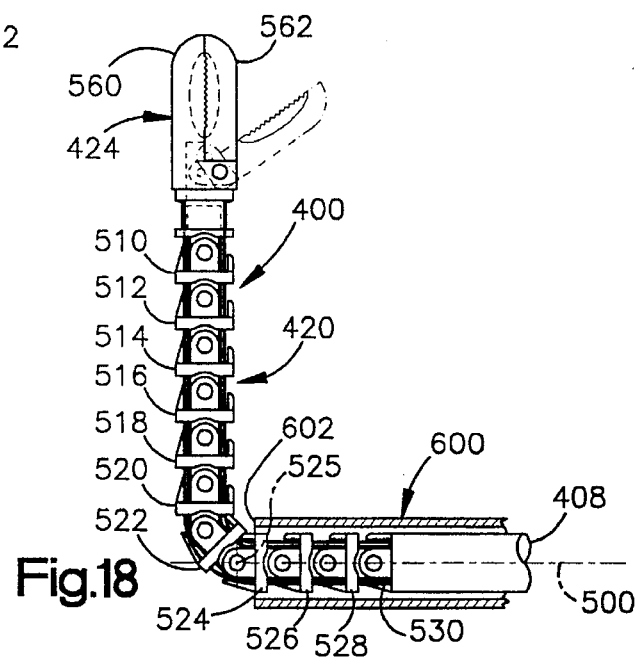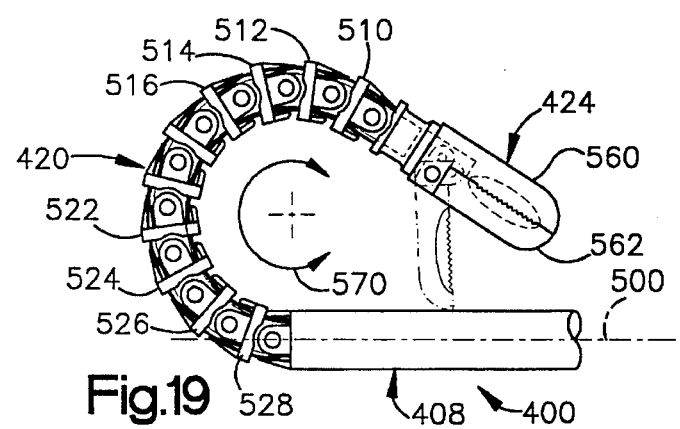

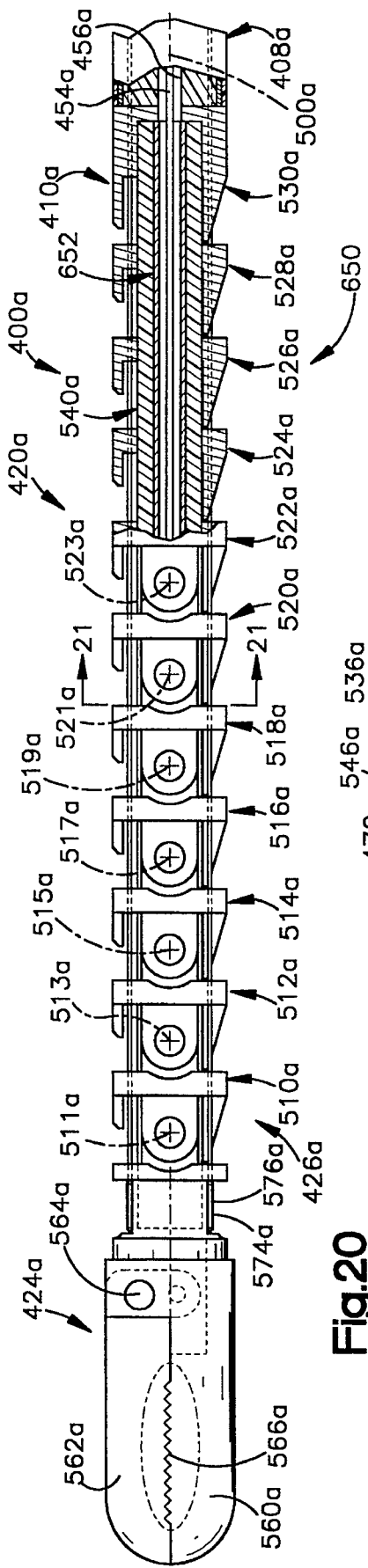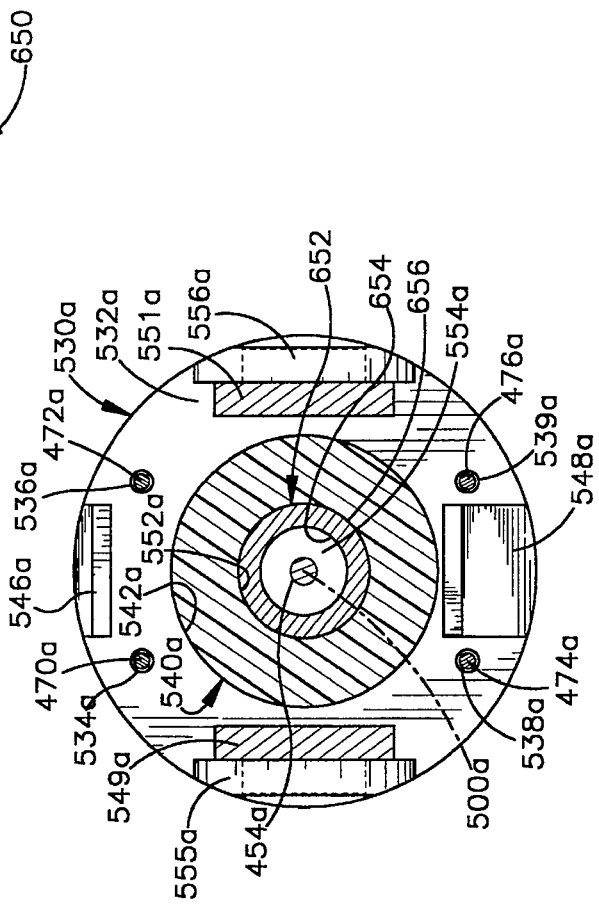

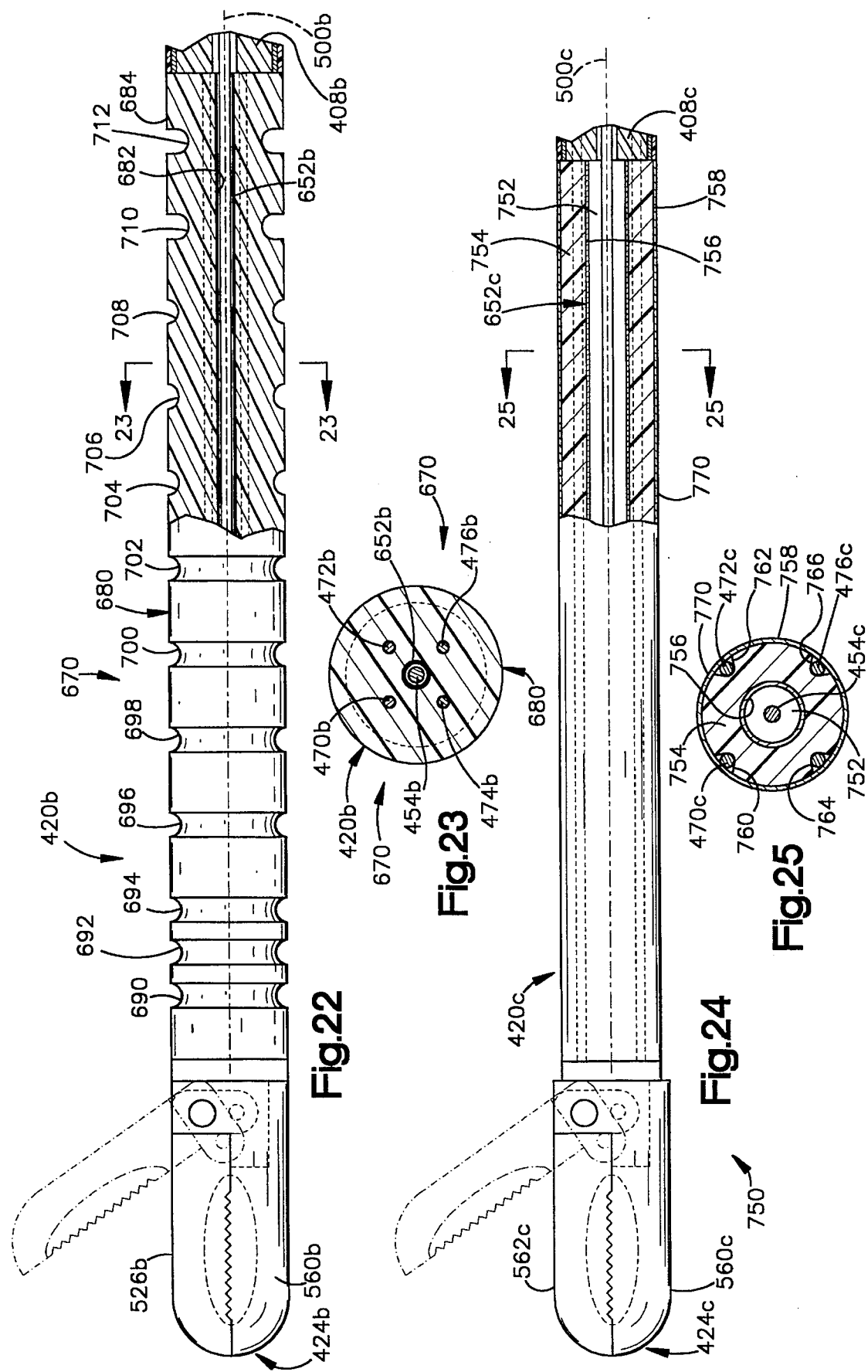

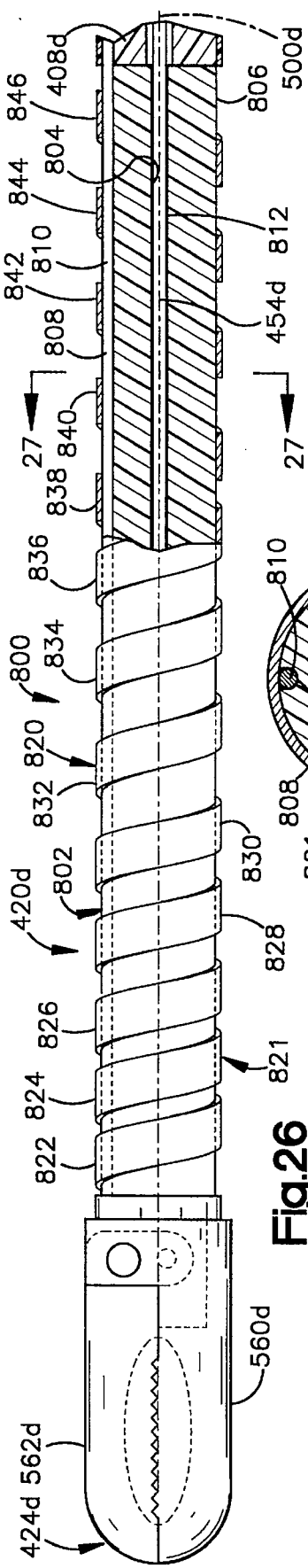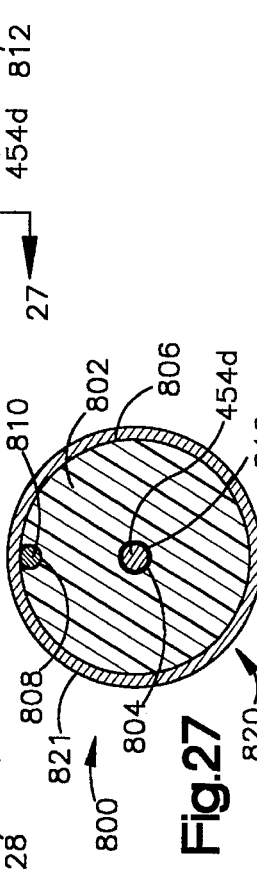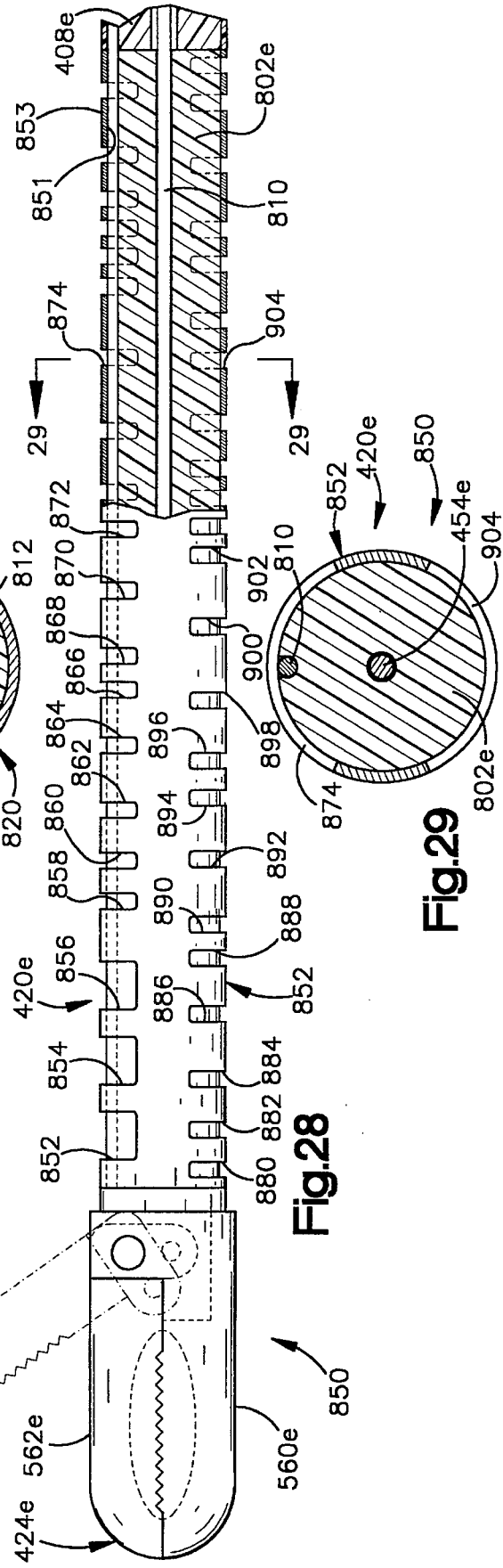

5,618,294

SURGICAL INSTRUMENT

RELATED APPLICATIONS

This application is a continuation-in-part of U.S. patent application Ser. No. 08/248,507, filed May 24, 1994, now U.S. Pat. No. 5,454,827.

BACKGROUND OF THE INVENTION

The present invention relates to a surgical instrument and more particularly, to an arthroscopic/endoscopic surgical instrument which may be used to remove or otherwise treat tissue in a joint or other body space or a potential space.

Surgical instruments which may be used to remove tissue or perform other operations on tissue are disclosed in U.S. Pat. Nos. 4,499,899; 4,517,977; 4,649,919; 4,763,669; and 4,834,729. The surgical instruments disclosed in these patents have stem sections which extend outwardly from a handle. A cutting tool or other device is disposed at the outer end of the stem section. The stem section is rigid, and the cutting tool or other device can not be moved in different planes relative to the stem section. Other surgical instruments, in which a cutting tool is movable relative to the stem section, are shown, for example, in U.S. Pat. Nos. 5,354,311, 5,330,502, 5,209,747, and 5,152,744.

SUMMARY OF THE INVENTION

In a first embodiment, the present invention is a surgical instrument comprising a manually engageable handle, a rigid stem section extending from the handle, and a tissue engaging means for engaging tissue. The tissue engaging means includes first and second tissue engaging members. The first tissue engaging member is pivotable relative to the second tissue engaging member to engage tissue between the first and second tissue engaging members. An articulated shaft is connected between the stem section and the tissue engaging means, and supports the tissue engaging means for movement between a plurality of orientations relative to the stem section. First actuator means is connected with the handle for bending the articulated shaft to change the orientation of the tissue engaging means relative to the stem section from a first orientation to a second orientation. Second actuator means is connected with the handle and with the first tissue engaging member for effecting pivotal movement of the first tissue engaging member relative to the second tissue engaging member to engage tissue between the first and second tissue engaging members when the tissue engaging means is in any of its plurality of orientations relative to the stem section.

In another embodiment, the present invention is a surgical instrument comprising a manually engageable handle, a first stem section having a longitudinal axis and extending from the handle, and tissue engaging means for engaging tissue. The tissue engaging means includes at least a first tissue engaging member. A second stem section is connected between the first stem section and the tissue engaging means. The second stem section has at least a portion which is bendable and supports the tissue engaging means for movement between a plurality of orientations relative to the axis and to the first stem section. The surgical instrument includes means for supporting the first tissue engaging member on the bendable portion of the second stem section, and means for bending the bendable portion of the second stem section to change the orientation of the tissue engaging means relative to the axis and to the first stem section from a first orientation to a second orientation. The bendable portion of the second stem section comprises means for enabling bending movement of the bendable portion to locate the tissue engaging means in an orientation extending 90° to the longitudinal axis of the first stem section at more than one location along the length of the bendable portion.

BRIEF DESCRIPTION OF THE DRAWINGS

Further features of the present invention will become apparent to those skilled in the art to which the present invention relates from reading the following specification with reference to the accompanying drawings, in which:

FIG. 3 is an enlarged schematic side elevational view of an articulated stem section of the surgical instrument of FIG. 1;

FIG. 4 is an enlarged schematic top plan view of the articulated section;

FIG. 5 is a schematic illustration depicting deflection of the articulated section in one of four directions;

FIG. 5a is a schematic view of a portion of FIG. 5 showing the articulated section bent in a first direction;

FIG. 5b is a view similar to FIG. 5a showing the articulated section bent in a second direction;

FIG. 5c is a view similar to FIG. 5a showing the articulated section bent in a third direction;

FIG. 5d is a view similar to FIG. 5a showing the articulated section bent in a fourth direction;

FIG. 10 is a schematic side elevational view of a surgical instrument constructed in accordance with a sixth embodiment of the present invention;

FIG. 11 is an enlarged view of a portion of FIG. 10;

FIG. 12 is a sectional view taken along line 12—12 of FIG. 10;

FIG. 13 is an enlarged schematic side elevational view of a movable stem section of the surgical instrument of FIG. 10;

FIG. 14 is a sectional view taken along line 14—14 of FIG. 13;

FIG. 15 is a fragmentary plan view taken along line 15—15 of FIG. 13;

FIG. 16 is a schematic view of a portion of FIG. 10 showing the movable stem section associated with a cannula and bent in a first direction;

FIG. 17 is a view similar to FIG. 16 showing the movable section bent further and in a second direction;

FIG. 18 is a view similar to FIG. 17 showing the movable section of the surgical instrument bent at a different location along its length;

FIG. 19 is a view similar to FIG. 18 showing the movable section bent to an angle greater than 180°;

FIG. 20 is a view similar to FIG. 13 of a portion of a surgical instrument which is constructed in accordance with a seventh embodiment of the present invention;

FIG. 21 is a sectional view taken along line 21—21 of FIG. 20;

FIG. 22 is a view similar to FIG. 20 of a portion of a surgical instrument which is constructed in accordance with an eighth embodiment of the present invention;

FIG. 23 is a sectional view taken along line 23—23 of FIG. 22;

FIG. 24 is a view similar to FIG. 22 of a portion of a surgical instrument which is constructed in accordance with a ninth embodiment of the present invention;

FIG. 25 is a sectional view taken along line 25—25 of FIG. 24;

FIG. 26 is a view similar to FIG. 24 showing a portion of a surgical instrument which is constructed in accordance with a tenth embodiment of the present invention;

FIG. 27 is a sectional view taken along line 27—27 of FIG. 26;

FIG. 28 is a view similar to FIG. 26 showing a portion of a surgical instrument which is constructed in accordance with an eleventh embodiment of the present invention;

FIG. 29 is a sectional view taken along line 29—29 of FIG. 28;

DESCRIPTION OF PREFERRED EMBODIMENT

Figure 1:
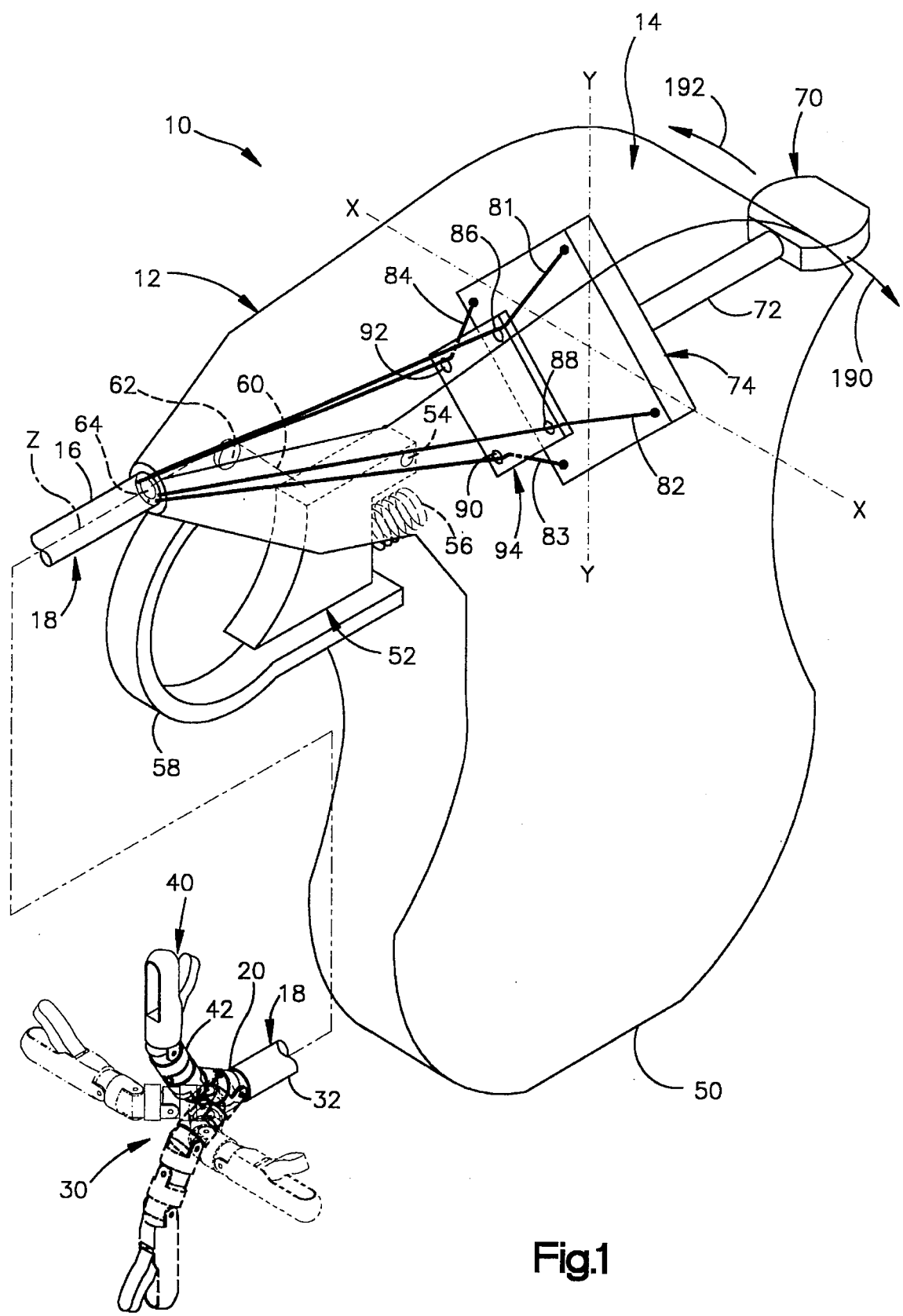
FIG. 1 is a schematic illustration of a surgical instrument constructed in accordance with the present invention.

The present invention relates to a surgical instrument and in particular to a surgical instrument which may be used to remove tissue or perform other operations on tissue. The present invention is applicable to various surgical instrument constructions. As representative of the present invention, FIG. 1 illustrates a surgical instrument 10.

The surgical instrument 10 includes generally a handle 12 with an actuator assembly 14. A proximal end portion 16 of a rigid stem section 18 is fixed to the handle 12. A proximal end portion 20 of an articulated stem section 30 is connected with a distal end portion 32 of the rigid stem section 18. A basket cutter 40 is connected with a distal end portion 42 of the articulated stem section 30.

The handle 12 (FIG. 1) includes a main body portion 50 which is configured to be manually gripped by a person's hand. A trigger 52 is connected at 54 to the main body portion 50 for pivotal movement relative to the main body portion. A spring 56 connected between the trigger 52 and the main body portion 50 biases the trigger to an unactuated position shown in FIG. 1. A trigger guard 58 blocks unintended contact with the trigger 52.

A proximal end portion of a control wire 60 is connected with the trigger 52. The control wire 60 extends from the trigger 52 over a guide indicated schematically at 62 and thence into a central passage 64 in the rigid stem section 18. The control wire 60, in a manner to be described below, extends through the rigid stem section 16 and through the articulated stem section 30 and is connected with the basket cutter 40.

The actuator assembly 14 is mounted in the main body portion 50 of the handle 12. The actuator assembly 14 is illustrated only schematically. It should be understood that other types of actuator assemblies capable of providing the multi-directional control provided by the actuator assembly 14 can be substituted. Thus, the actuator assembly 14 is illustrative of the various types of actuator assemblies which can be used to provide the actuation force for bending the articulated stem section 30 in multiple planes as indicated in FIG. 1.

The actuator assembly 14 (FIGS. 1 and 2) includes a control lever 70 which projects from the handle main body portion 50. The control lever 70 is supported by a rod 72 which is fixed for movement with a control plate 74. The control plate 74 is mounted in the handle main body portion 50 in a suitable manner, not shown, for simultaneous pivotal movement about both an X axis and a perpendicular Y axis as indicated in FIG. 1.

The proximal ends of four actuator wires 81, 82, 83, and 84 are fixed to respective corners of the control plate 74. The four actuator wires 81, 82, 83, and 84 extend through respective guide openings 86, 88, 90, and 92 in a guide plate 94. The guide plate 94 is fixed in position in the handle main body portion 50 in a manner not shown. The actuator wires 81–84 extend from the guide plate 94 into the central passage 64 in the rigid stem section 18. The actuator wires 81–84, in a manner to be described below, pass through the rigid stem section 18 and are connected with the basket cutter 40 which is mounted on the end of the articulated stem section 30.

The rigid stem section 18 is a hollow tubular member which extends between and interconnects the handle 12 and the articulated stem section 30. The rigid stem section 16 is cylindrical in configuration with parallel cylindrical inner and outer surfaces 96 and 98. The cylindrical inner surface 96 defines the central passage 64 in the rigid stem section 16. The control wire 60 and the four actuator wires 81, 82, 83, and 84 extend through the central passage 64 of the rigid stem section 16. The rigid stem section 16 defines a Z axis of the surgical instrument 10 which extends perpendicular to the X and Y axes.

The articulated stem section 30 is made of a plurality of links which are pivotally interconnected to enable controlled movement of the basket cutter 40 in any selected direction and to any position off the Z axis. The links are rigid, generally cylindrical hollow members through which the control wire 60 and the actuator wires 81–84 extend.

The plurality of links in the articulated stem section 30 includes a first link 110 which is connected by a first pivot joint 112 to the distal end portion 32 of the rigid stem section 18. The first pivot joint 112 defines a first pivot axis 114 which, when the articulated stem section 30 is linear and extends along the Z axis, extends in a direction parallel to the X axis and perpendicular to the Z axis.

A second link 120 is connected by a second pivot joint 122 to the first link 110. The second pivot joint 122 defines a second pivot axis 124. When the articulated stem section 30 is linear and is aligned along the Z axis, the second pivot axis 124 extends in a direction parallel to the Y axis and perpendicular to the Z axis.

A third link 130 is connected by a third pivot joint 132 to the second link 120. The third pivot joint 132 defines a third pivot axis 134 which extends in a direction parallel to the first pivot axis 114.

A fourth link 140 is connected by a fourth pivot joint 142 to the third link 130. The fourth pivot joint 142 defines a fourth pivot axis 144 which extends in a direction parallel to the second pivot axis 124.

The basket cutter 40 is connected by a fifth pivot joint 150 to the fourth link 140. The fifth pivot joint 150 defines a fifth pivot axis 152 which extends in a direction parallel to the first pivot axis 114.

The basket cutter 40 includes a fixed jaw 160 and a movable jaw 162. A pivot joint 164 connects the movable jaw 162 with the fixed jaw 160 for pivotal movement relative to the fixed jaw.

The fixed jaw 160 includes a side wall 166 which defines an open-ended chamber 168 in the fixed jaw. The movable jaw 162 includes a side wall 170 which extends around and defines a chamber 172. The side wall 170 has a cutting edge 174 presented toward the side wall 166 of the fixed jaw 160. The fixed jaw 160 and the movable jaw 162 define between them a mouth or gap 180 within which human tissue can be received and grasped upon pivotal movement of the movable jaw toward the fixed jaw.

The four actuator wires 81–84 extend through the open centers of the links 110, 120, 130, and 140. The distal ends of the actuator wires 81–84 are connected with the fixed jaw 160 of the basket cutter 40. The wires 81–84 are connected at locations evenly spaced 90° apart around the periphery of the fixed jaw 160. Directional movement and positioning of the basket cutter 40 via the articulated stem section 30 are controlled by the tension on the actuator wires 81–84 as set by the actuator assembly 14.

Figure 2:
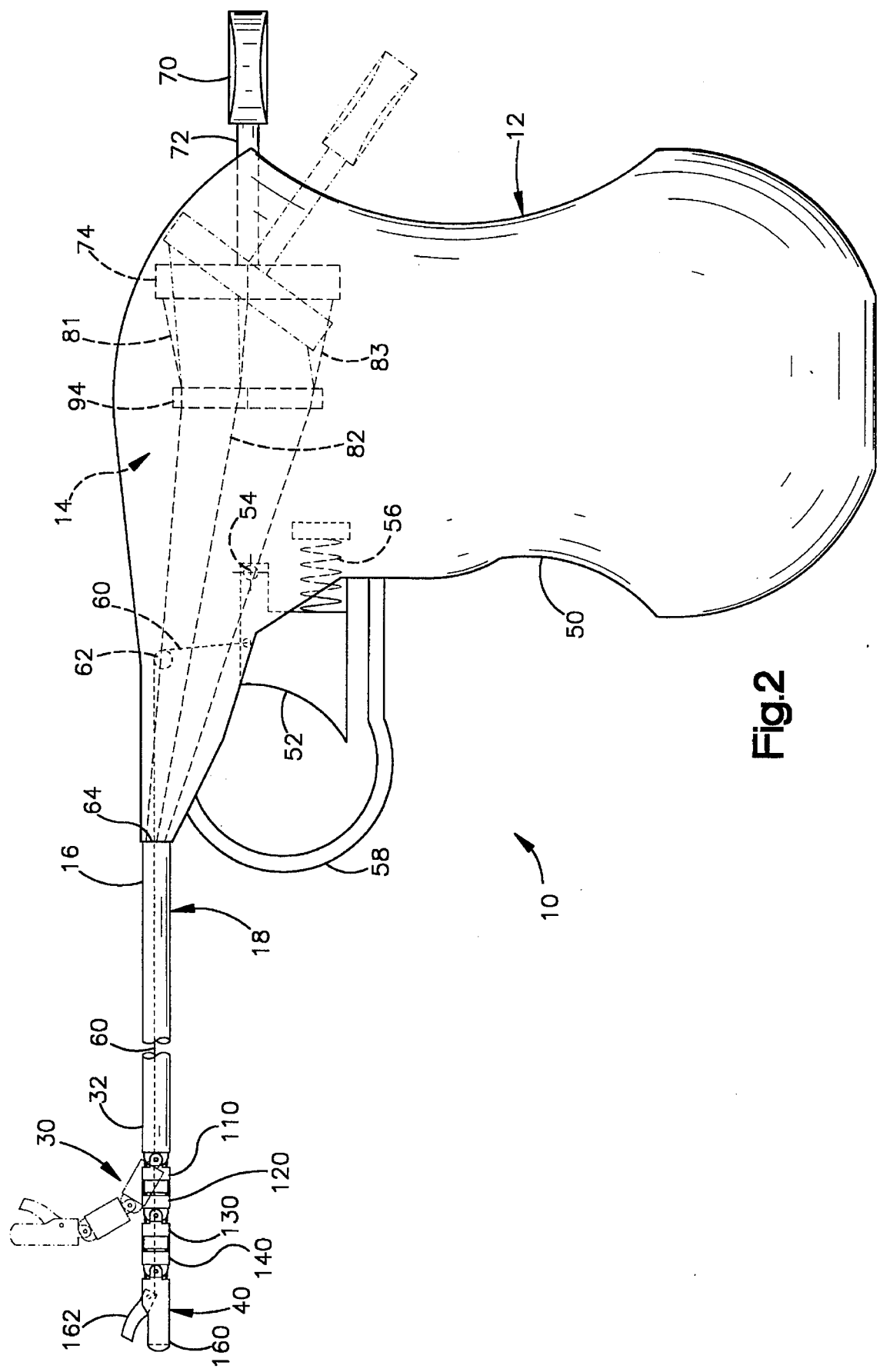
FIG. 2 is a schematic side elevational view of the instrument of FIG. 1.

Thus, when the control lever 70 (FIGS. 1 and 2) is in the centered position shown in solid lines in FIG. 2, the articulated stem section 30 is linear, and it and the basket cutter 40 are aligned along the Z axis as shown in FIG. 5. Downward movement of the control lever 70 as seen in FIG. 1 and 2, from the position shown in solid lines in FIG. 2 to the position shown in dashed lines in FIG. 2, causes the control plate 74 to pivot relative to the handle main body portion 50 about the X axis (FIG. 1). This pivoting movement of the control plate 74 tensions the actuator wire 81 and releases the tension on the opposite actuator wire 83. This change in the tension on the wires 81 and 83 is transmitted through the wires 81 and 83 into the basket cutter 40. The increase in tension on the wire 81 acts to attempt to pull the basket cutter 40 toward the handle 12. The articulated stem section 30 bends as the links 110, 120, 130, and 140 pivot relative to the rigid stem section 30. The fixed jaw 160 of the basket cutter 40 thus moves upward off the Z axis in a direction toward the Y axis.

If the control lever 70 is, in this manner, moved to its lowest position, the basket cutter 40 moves to its highest position, aligned with the Y axis, as illustrated in solid lines in FIG. 5 and as also illustrated in FIG. 5a. The basket cutter 40 is, by appropriate positioning of the control lever 70 within its range of pivoting movement about the X axis, movable to any position between the aligned position along the Z axis and the full upward position shown in FIG. 5a. This occurs as a result of the bending of the articulated stem section 30.

If the control lever 70 is moved in the opposite direction, the basket cutter 40 moves also in the opposite direction.

Thus, movement of the control lever 70 in an upward direction as viewed in FIGS. 1 and 2, from the position shown in solid lines in FIG. 2, causes the control plate 74 to pivot relative to the handle main body portion 50 about the X axis (FIG. 1). This pivoting movement of the control plate 74 tensions the actuator wire 83 and releases the tension on the opposite actuator wire 81. This change in the tension of the wires 81 and 83, whose ends are connected with the fixed jaw 160 of the basket cutter 40, causes the basket cutter to move downward off the Z axis in a direction toward a position as shown in FIG. 5c. The position of the control lever 70 is continuously adjustable among a plurality of positions between the position aligned with the Z axis as shown in FIG. 2 in solid lines and its uppermost position. As described above, the position of the basket cutter 40 is also continuously adjustable between a position aligned with the Z axis and a lowermost position as illustrated in FIG. 5c, and any position in between.

In a similar manner, horizontal movement of the control lever 70 relative to the handle main body portion 50 results in corresponding horizontal movement of the basket cutter 40. Thus, movement of the control lever 70 in the direction indicated by the arrow 190 (FIG. 1) causes the control plate 74 to pivot about the Y axis (FIG. 1). The tension on the actuator wire 84 is increased and, simultaneously, tension on the actuator wire 82 is decreased. These changes in tension of the actuator wires are transmitted into the fixed jaw 160 of the basket cutter 40. The articulated stem section 30 bends and the basket cutter 40 moves horizontally, that is, in the plane defined by the X and Z axes as illustrated in FIG. 5, toward the position illustrated in FIG. 5d. The range of movement of the basket cutter 40 in this direction is continuous, so the basket cutter 40 can be placed in any position between a position aligned with the Z axis and a position aligned with the X axis as illustrated.

Again, movement of the control lever 70 in the opposite direction as indicated by the arrow 192 in FIG. 1 tensions the actuator wire 82 and releases the tension on the actuator wire 84. The change in tension on the actuator wires 82 and 84 is transmitted to the fixed jaw 160 of the basket cutter 40. The articulated stem section 30 bends and the basket cutter 40 moves in the plane defined by the X and Z axes from a position aligned with the Z axis toward a position aligned with the X axis. The basket cutter may, by appropriate positioning of the control lever 70, be placed in any position between a position aligned with the Z axis and a position aligned with the X axis as illustrated in FIG. 5b.

It should be understood that any combination of the foregoing four movements is possible. Thus, the basket cutter 40 is movable not only in the planes illustrated in FIGS. 5–5d but also to any intermediate position in any combination of the planes. The basket cutter 40 can be moved upward while it is being moved to the left or right. The basket cutter 40 can be moved downward while it is being moved to the left or right.

The positioning of the movable jaw 162 of the basket cutter 40 relative to the fixed jaw 160 is controlled by tension on the control wire 60 as set by the trigger 52. When the trigger 52 is in the unactuated position as illustrated in FIGS. 1 and 2, the tension on the control wire 60 is lowest and the basket cutter 40 is open. The movable jaw 162 is biased by a spring (not shown) to an open position as illustrated in the Figures spaced apart from the fixed jaw 160 and defining between them a gap 180.

To cut or remove tissue with the basket cutter 40, the basket cutter is maneuvered so that the tissue is disposed in the gap 180 between the fixed and movable jaws 160 and 162. The trigger 52 is pulled, against the bias of the spring 56. The trigger 52 pivots about the pivot axis 54, tensioning the control wire 60. The distal end of the control wire 60 is connected with the movable jaw 162 of the basket cutter 40, as illustrated in FIG. 3. Tensioning of the control wire 60 thus results in pivotal movement of the movable jaw 162 from the open position shown in FIG. 3 to a closed position (not shown).

Tissue which is during this movement disposed in the gap 180 is engaged by the cutting edge 174 on the side wall 170 of the movable jaw 162. The cutting edge 174 on the side wall 170 of the movable jaw 162 slides against the side wall 166 of the fixed jaw 160. The basket cutter 40 can then be removed from the operating location to gain access to the tissue. Releasing the pressure on the trigger 52 causes the trigger to return to the position shown in FIG. 1 under the influence of the spring 56. This lowers the tension on the control wire 60. The basket cutter 40 opens and releases the tissue.

It should be understood that the basket cutter 40 is actuatable independently of its position as set by the articulated stem section 30. Thus, the movable jaw 162 may be moved relative to the fixed jaw 160 regardless of the overall position of the basket cutter 40 as set by the articulated stem section 30. It should also be understood that the surgical instrument 10 is preferably used in arthroscopic or endoscopic surgery to remove or treat human tissue at subsurface locations such as in a knee joint or in the spine.

Figure 6:
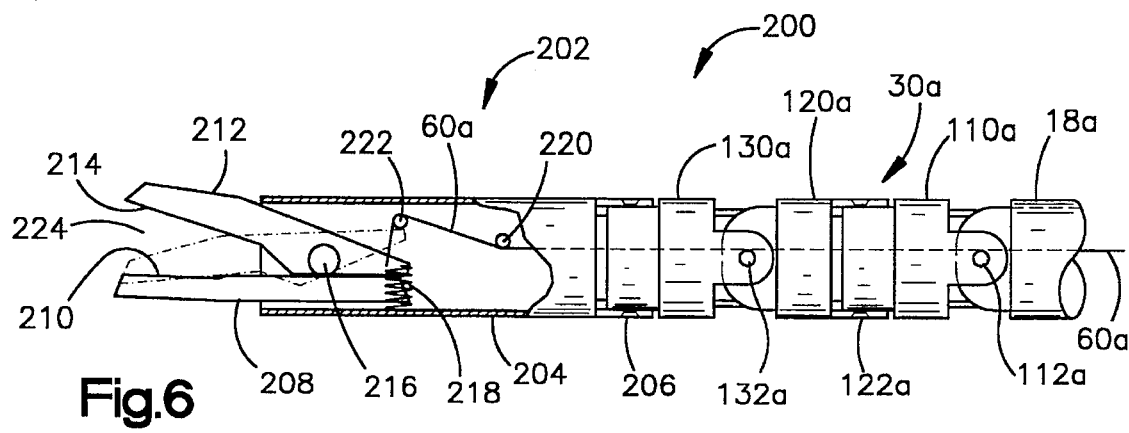
FIG. 6 is a schematic side view, partly in section, showing a second surgical instrument, which includes a scissors assembly mounted on an articulated section.

FIG. 6 illustrates a surgical instrument 200 in accordance with a second embodiment of the present invention. In place of the basket cutter 40, the surgical instrument 200 includes a scissors assembly 202 mounted on the end of an articulated stem section 30a. The articulated stem section 30a is identical to the articulated stem section 30 illustrated in FIGS. 1–5.

The scissors assembly 202 includes a base 204 connected by a pivot joint 206 to a link 130a of the articulated stem section 30a. A fixed blade 208 is rigidly mounted on the base 204. The fixed blade 208 has a cutting edge 210. A movable blade 212 having a cutting edge 214 is pivotally mounted at 216 to the base 204. A spring 218 biases the movable blade 212 away from the fixed blade 208 to an open position as illustrated in FIG. 6.

A control wire 60a extends through the open center of the articulated stem section 30a. The control wire 60a is trained over pins 220 and 222 and is connected with the movable blade 212. Tensioning the control wire 60a causes pivotal movement of the blade 212 from the open position shown in solid lines in FIG. 6 to the cutting position shown in dot-dash lines. Tissue which is disposed in the gap 224 between the blades 208 and 212 is cut during such pivotal movement. Upon release of tension on the control wire 60a, the spring 218 moves the movable blade 212 back to the open position. Pivotal movement of the movable scissors blade 212 in either direction can be accomplished in any position of orientation of the scissors assembly 202 as provided by the bending of the articulated stem section 30a.

Figure 7:
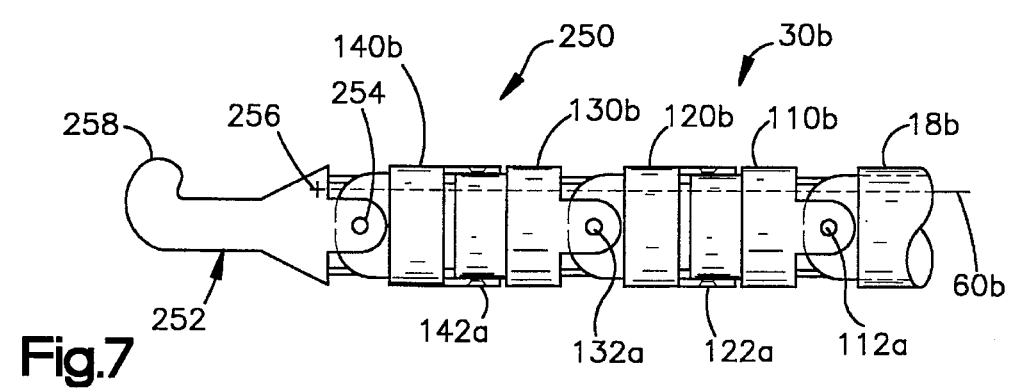
FIG. 7 illustrates a surgical instrument including a probe or knife mounted on an articulated section.

FIG. 7 illustrates a surgical instrument 250 in accordance with a third embodiment of the invention. The surgical instrument 250 includes an articulated stem section 30b which is identical to the articulated stem section 30 illustrated in FIGS. 1–5. A one-piece instrument 252 which can be either a probe or a knife is mounted on the end of the articulated stem section 30b. A pivot joint 254 provides for pivotal movement of the instrument 252 relative to the final link 140b of the articulated stem section 30b. A control wire indicated schematically at 60b extends through the open center of the links into the articulated stem section 30b. The control wire 60b terminates at a connection 256 fixed to the instrument 252.

Upon tensioning the control wire 60b, the instrument 252 pivots about the pivot joint 254 in an upward direction as viewed in FIG. 7. Upon release of tension on the control wire 60b, a spring or other biasing means (not shown) returns the instrument 252 to its illustrated position. The instrument 252 is actuatable in this manner when in any position of orientation of the articulated stem section 30b.

If the instrument 252 is a knife, it possesses a cutting edge as indicated at 258. Alternatively, any other one-piece instrument in the nature of a probe or a knife could be substituted.

Figure 8:
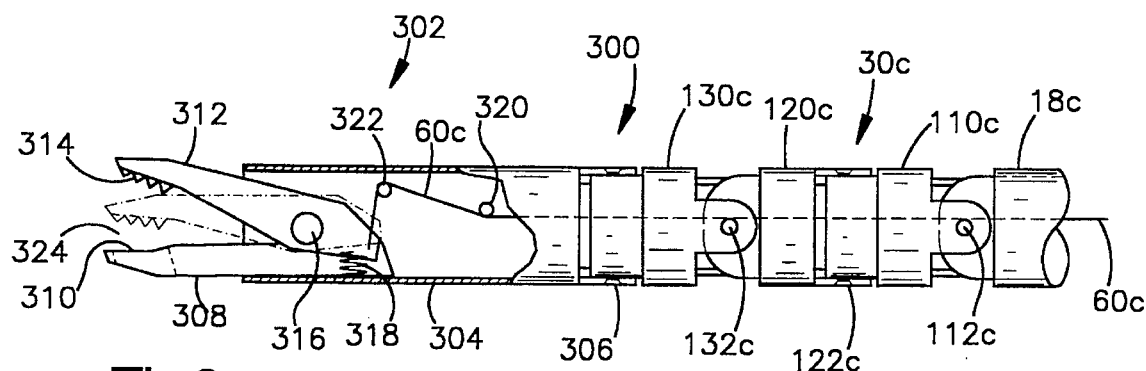
FIG. 8 illustrates a surgical instrument including a basket cutter of an alternative construction mounted on the articulated section.

FIG. 8 illustrates a surgical instrument 300 in accordance with a fourth embodiment of the invention. The surgical instrument 300 includes a basket cutter 302 mounted on a distal end of an articulated stem section 30c. The articulated stem section 30c is identical to the articulated stem section 30 illustrated in FIGS. 1–5. The basket cutter 302 differs somewhat from the basket cutter 40 illustrated in FIGS. 1–5.

The basket cutter 302 includes a base 304 connected by a pivot joint 306 to the final link 130c of the articulated stem section 30c. A jaw 308 is fixed to the base 304. The fixed jaw 308 has an open cutting area indicated schematically at 310. The basket cutter 302 includes a movable jaw 312 having cutting teeth indicated schematically at 314. The movable jaw 312 is connected at a pivot joint 316 for pivotal movement relative to the fixed jaw 308. A spring 318 biases the movable jaw 312 into an open position as illustrated in solid lines in FIG. 8.

A control wire 60c is trained around pins 320 and 322 fixed to the base 304 and is connected with the movable jaw 312. Tension on the control wire 60c pivots the movable jaw 312 from the position shown in solid lines in 312, against the biasing effect of the spring 318, and into a position adjacent the fixed jaw 308. Tissue which is during this pivotal movement disposed in the gap 324 between the teeth 314 and the open area 310 is cut and retained in the basket.

The basket cutter 302 may then be withdrawn from the body. Release of tension on the control wire 60c results in movement of the movable jaw 312, under the influence of the biasing spring 318, into the open position to allow removal of the captured tissue. The basket cutter 302 is actuatable between the open and closed positions when in any orientation of the articulated stem section 30c.

Figure 9:
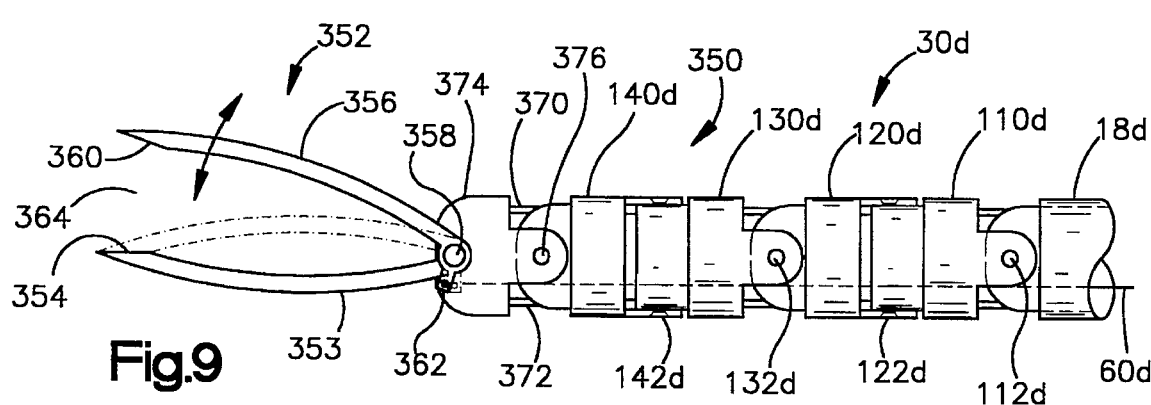
FIG. 9 illustrates a surgical instrument including a forceps/grasper assembly mounted on the articulated section.

FIG. 9 illustrates a surgical instrument 350 in accordance with a fifth embodiment of the invention. The surgical instrument 350 includes a forceps/grasper assembly 352 connected to the distal end portion of a articulated stem section 30d. The articulated stem section 30d is identical to the articulated stem section 30 illustrated in FIGS. 1–5. The forceps/grasper assembly 352 include a fixed jaw 353 having a grasping surface 354. A movable jaw 356 is pivotally connected at 358 to the fixed jaw 353. The movable jaw 356 has a grasping surface 360 which is opposable to the grasping surface 354 on the fixed jaw 353. A control wire 60d is connected to a tab 362 fixed to the movable jaw 356.

Tensioning of the control wire 60d results in pivotal movement of the movable jaw 356 from the position shown in solid lines in FIG. 9 to the position shown in dot-dash lines in FIG. 9. During such pivotal movement, tissue which is disposed in a gap 364 between the grasping surfaces 354 and 360 is captured between the fixed and movable jaws 353 and 356. The forceps/grasper assembly 352 is actuatable regardless of the orientation of the articulated stem section 30*d*.

Actuator wires 370 and 372 (FIG. 9) are connected with a base 374 of the forceps/grasper assembly 352. The actuator wires 370 and 372 are movable, in a manner as described with reference to FIGS. 1–5, to position the forceps/grasper assembly 352 about an axis relative to the final link 140*d* of the articulated stem section 30*d*. Appropriate tensioning of the actuator wires 370 and 372 causes the forceps/grasper assembly 352 to pivot as a whole about a pivot connection 376 upward or downward as viewed in FIG. 9. Another pair of actuator wires (not shown) are connected with the base 374 to move the forceps/grasper assembly 352 to any selected position along a range of movement on a perpendicular axis.

In a similar manner, the surgical instruments illustrated in FIGS. 6, 7, and 8 are also freely positionable in the manner illustrated in FIG. 5. To this end, four actuator wires (not shown) are connected to the base 204 (FIG. 6) of the scissors assembly 202. Four actuator wires (not shown) are connected with the final link 140*b* (FIG. 7) of the articulated stem section 30*b* to move the final link and thereby the instrument 252, together, relative to the rigid stem section 16*b*. And in FIG. 8, four actuator wires (not shown) are connected with the base 304 of the basket cutter 302. The actuator wires of these devices are operable in the manner described with reference to FIGS. 1–5 to bend the articulated stem section 30*b*–30*d* to position the instruments with which they are connected.

FIGS. 10–19 illustrate a surgical instrument 400 which is constructed in accordance with a sixth embodiment of the present invention. The surgical instrument 400 includes generally a handle 402 with an actuator assembly 404. A proximal end portion 406 of a first stem section or rigid stem section 408 is fixed to the handle 402. A proximal end portion 410 of a second or movable stem section 420 is connected with a distal end portion 422 of the rigid stem section 408. A pituitary rongeur (grasper) 424 is connected with a distal end portion 426 of the movable stem section 420.

The handle 402 includes a main body portion 430 having a pistol grip configuration which is configured to be manually gripped by a person's hand. A trigger 432 is supported by a pivot pin 434 on the main body portion 430 of the handle 402 for pivotal movement relative to the main body portion. A spring 436 connected between the trigger 432 and the main body portion 430 of the handle 402 biases the trigger to an unactuated position shown in FIG. 10.

A transfer plate 440 is supported at 442 on the main body portion 430 of the handle 402 for pivotal movement relative to the main body portion of the handle. A first end portion 444 of the transfer plate 440 is received in a recess 446 in the trigger 432. An opposite second end portion 448 of the transfer plate 440 is connected with a proximal end portion 450 of a pull wire 454. The pull wire 454 extends from the transfer plate 440 into a central passage 456 (FIG. 12) in the rigid stem section 408. The pull wire 454, in a manner described below, extends through the rigid stem section 408 and through the movable stem section 420 and is connected with the pituitary rongeur 424 for actuation of the pituitary rongeur.

The actuator assembly 404 is mounted in the main body portion 430 of the handle 402. The actuator assembly 404 is illustrated only schematically. It should be understood that other types of actuator assemblies can be substituted. Thus, the actuator assembly 404 is illustrative of the various types of actuator assemblies which can be used to provide the actuation force for bending the movable stem section 420 of the surgical instrument 400 in a manner as indicated in FIGS. 16–19.

The actuator assembly 404 (FIGS. 10 and 11) includes a deflection control lever 460 which projects from the main body portion 430 of the handle 402. The deflection control lever 460 is supported by a pivot pin 462 for pivotal movement relative to the main body portion 430 of the handle 402. A spring 464 connected between the deflection control lever 460 and the main body portion 430 of the handle 402 biases the deflection control lever into the unactuated position shown in FIG. 10.

The proximal ends of four deflection control wires 470, 472, 474, and 476 (FIGS. 11 and 12) are connected for movement with the deflection control lever 460. The deflection control wires 470–476 extend from the deflection control lever 460 into respective deflection control wire passages 480–486 (FIG. 12) in the rigid stem section 408. The deflection control wires 470–476, in a manner described below, pass through the rigid stem section 408 and are connected with the distal end portion 426 of the movable stem section 420.

The rigid stem section 408 (FIG. 12) is a tubular member which extends between and interconnects the handle 402 and the movable stem section 420. The rigid stem section 408 includes a generally cylindrical main body portion 490 (FIG. 12) which is made from a plastic material and which has parallel cylindrical inner and outer surfaces 492 and 494. The central passage 456 of the rigid stem section 408 is defined by the inner peripheral surface 492 of the body portion 490. The deflection control wire passages 480–486 are formed in the outer surface 494 of the main body portion 490. A metal sheath 496 overlies the main body portion 490. A plastic outer sheath 498 overlies the metal sheath 496. The rigid stem section 408 has a longitudinal central axis 500 which forms a longitudinal central axis of the surgical instrument 400.

It should be noted that the rigid stem section 408 may have a construction other than as illustrated. For example, the main body portion 490 may be omitted and a radially thicker metal sheath 496 provided, with the deflection control wires 470–476 extending through grooves formed on the outer periphery of the thicker metal sheath 496. Other configurations are also possible.

The movable stem section 420 (FIG. 13) is made of a plurality of links 510–530 which are pivotally interconnected to enable controlled movement of the pituitary rongeur 424 to a plurality of positions off the axis 500 as illustrated, for example, in FIGS. 16–19. The links 510–530 are generally similar in function and construction to the links 110–140 (FIGS. 1–9) illustrated with respect to the first embodiment of the invention.

Each link 510–530 is preferably made from a metal such as stainless steel and includes a radially extending wall portion 532 having four deflection control wire passages 534, 536, 538, and 539 through which the deflection control wires 470–476 extend. The wall portion 532 of each link 510–530 also includes a circular central opening 542 centered on the axis 500. Upper and lower guide tabs 546 and 548 project axially from the main body portion 532 of each link 510–530 in a direction toward the pituitary rongeur 424.

On each link 510–530, a pair of pivot pins 549 and 551 are received in socket portions 555 and 556 of the next most proximal link. The pivot pins 549–551 and the sockets 555–556 define a plurality of pivot axes 510*a*–530*a* which extend in a direction perpendicular to the central axis 500 and parallel to each other. Each pivot axis, in the preferred embodiment, provides about 45° of relative movement between an adjacent pair of links. This amount of movement could be different in other configurations in accordance with the present invention. The most proximal link 530 of the movable stem section 420 is rigidly connected with the rigid stem section 408.

The movable stem section 420 also includes a plastic body portion 540. The plastic body portion 540 is a flexible tubular member which extends within the central passages 542 of the links 510–530. The plastic body portion 540 has a generally cylindrical configuration with an inner periphery 552. The plastic body portion 540 is preferably made from a polymeric material such as polytetrafluoroethylene which is flexible and resilient.

The movable stem section 420 also includes a spring 550. The spring 550 is a metal coil spring with zero pitch, that is, with no distance between adjacent turns of the wire from which the spring 550 is formed. The spring 550 is closely fitted within the inner periphery 552 of the plastic body portion 540 of the movable stem section 420. The spring 550 and the plastic body portion 540 are axially coextensive with the links 510–530.

The spring 550 defines a cylindrical central passage 554 of the movable stem section 420. The central passage 554 is centered on the axis 500 when the movable stem section 420 is linear as shown in FIG. 13. The pull wire 454 extends through the central passage 554 in the movable stem section 420.

The pituitary rongeur 424 is connected with the outermost or most distal link 510 of the movable stem section 420. The pituitary rongeur 424 includes a fixed jaw 560 and a movable jaw 562. A pivot joint 564 connects the movable jaw 562 with the fixed jaw 560 for pivotal movement relative to the fixed jaw. The pull wire 454 extends through the link 510 and is connected in a known manner (not shown) with the movable jaw 562 to move it relative to the fixed jaw 560 to engage tissue. Each of the fixed and movable jaws 560 and 562 includes a plurality of teeth serrations 566. The fixed jaw 560 and the movable jaw 562 define between them a mouth or gap 568 (FIG. 16) within which human tissue can be received and grasped upon pivotal movement of the movable jaw toward the fixed jaw.

The distal ends of the four actuator wires 470–476 are connected in a force-transmitting relationship with the fixed jaw 560 of the pituitary rongeur 424. In the preferred embodiment, the two upper (as viewed in FIGS. 1014) deflection control wires 470 and 472 are formed as one piece and include an intermediate portion 570 which loops around a post 572 (FIG. 15) on the fixed jaw 560 of the pituitary rongeur 424. In a similar manner, the two lower (as viewed in FIGS. 10–14) deflection control wires 474 and 476 are formed as one piece and include an intermediate portion 574 which loops around a post 576 (FIG. 13) on the fixed jaw 560 of the pituitary rongeur 424. Alternatively, the deflection control wires could extend through openings in the last bar (to the immediate right of the post 572 as viewed in FIG. 15) and loop around it, making the posts 572 and 576 unnecessary.

Directional movement and positioning of the pituitary rongeur 424 via the movable stem section 420 are controlled by the tension on the deflection control wires 470–476 as set by the actuator assembly 404. Thus, when the deflection control lever 460 (FIGS. 10 and 11) is in the unactuated position shown in FIG. 10, the movable stem section 420 is linear, and it and the pituitary rongeur 424 are aligned along the central axis 500 as shown in FIGS. 10 and 13. Downward movement (as viewed in FIGS. 10 and 11) of the deflection control lever 460, from the position shown in FIG. 10 to the position shown in FIG. 11, tensions the upper deflection control wires 470 and 472 and releases the tension on the lower deflection control wires 474 and 476. This change in the tension on the deflection control wires 470–476 is transmitted through the wires into the pituitary rongeur 424. The increase in tension on the upper control wires 470–472 acts to attempt to pull the pituitary rongeur 424 toward the handle 402. The movable stem section 420 bends about the pivot axes 510–530a as the links 510–530 pivot relative to the rigid stem section 408. The fixed jaw 560 and the pituitary rongeur 424 as a whole thus move upward (as viewed in FIGS. 10 and 16) off the central axis 500.

If the deflection control lever 460 is, in this manner, moved to its lowest position, and if the movement of the various links 510–530 of the movable stem section 420 is unrestricted, the pituitary rongeur 424 moves to the position shown in FIG. 19. In this position, the movable stem section 420 is bent through an arc 570 which is greater than 180°, relative to the central axis 500 of the surgical instrument 400.

The spring 550 provides a self-centering effect, thus helping to return the movable stem section 420 to its linear position upon release of the actuator 404. The spring 550 also provides a bearing surface for the pull wire 454. The tubular plastic body portion 540 supports and stabilizes the relatively movable links 510–530. The tubular plastic body portion 540 also has a self-centering effect.

The surgical instrument 400 is typically used in association with a cannula 600 (FIGS. 16–18) having an open distal end 602. The cannula 600 is a known tubular member of any suitable construction which is used, in a known manner, to provide an open path through body tissue to the operating site. Once the cannula 600 is properly positioned, the surgical instrument 400 is inserted axially through the cannula until at least the pituitary rongeur 424 protrudes from the distal end 602 of the cannula 600. A predetermined amount of the movable stem section 420 of the surgical instrument 400 may also protrude from the distal end 602 of the cannula 600, as described below.

When the surgical instrument 400 is thus inserted through the cannula 600, and the deflection control lever 460 is moved, the movable portion 420 of the second stem section 410 of the surgical instrument is bendable at about the location of the distal end 602 of the cannula 600, to position the pituitary rongeur 424 in the desired location. The distal end portion 602 of the cannula 600 acts as a fulcrum about which the surgical instrument bends. Depending on how much of the surgical instrument 400 protrudes from the distal end 602 of the cannula 600, the surgical instrument bends at different locations along its length. The surgical instrument 400 bends at different locations along the length of the movable stem section 420 because of the restrictions on its movement resulting from the presence of the cannula 600. Thus, the movable stem section of a surgical instrument in accordance with the present invention can be bent at the same angle relative to the longitudinal axis of the first stem section at more than one location along the length of the bendable portion.

For example, as shown in FIGS. 16 and 17, if only the two most distally located links 510 and 512 of the movable portion 420 protrude from the distal end 602 of the cannula 600, the surgical instrument 400 bends, as shown sequentially in FIGS. 16 and 17, at the approximate location of the pivot axis 513. The pituitary rongeur 424 as shown in FIG. 17 extends at an angle of 90° to the central axis 500, at the approximate location of the pivot axis 513.

In another example, if all of the links 510–524 protrude from the distal end 602 of the cannula 600, as shown in FIG. 18, the surgical instrument 400 bends in a manner as shown in FIG. 18. The presence of the cannula 600 causes the movable stem section 420 of the surgical instrument 400 to bend at the approximate location of the pivot axis 525. The pituitary rongeur 424 in FIG. 18 extends at an angle of 90° to the central axis 500, at the approximate location of the pivot axis 525. This location is spaced apart from the bending location shown in FIGS. 16 and 17 by a substantial distance along the length of the movable portion 420 of the second stem section 410 of the surgical instrument 400.

Thus, the positioning of the surgical instrument 400 relative to the cannula 600 can control and determine the bending location. It should be noted that, instead of a cannula, the wall of a body space can be used to control the bending. For example, the tough outer wall of a spinal disc can act as the fulcrum for bending the surgical instrument 400 to perform work within the spinal disc. Also, any of the embodiments described herein can be used with a cannula in the manner described above.

Further, the movable stem section 420 of the surgical instrument 400 can bend up to 90° to 180°, or more, at most any location along its length depending on the range of pivotal movement which is available at each pivot axis 511–531. For example, as shown in FIG. 19, the movable stem section 420 is bent through the arc 570 which has a circumferential extent of greater than 180°. The amount of bending of the movable stem section 420 of the surgical instrument 400 is controlled by the amount of tension on the deflection control wires 470–476 and the amount of movement of the deflection control lever 460.

Because of the ability of the surgical instrument to bend at 90° or more at almost any selected location along the length of the movable stem section 420, the pituitary rongeur 424 (or other tissue engaging member such as those shown in FIGS. 1–9 and 31–33) can be positioned and used in substantially any position outside the distal end 602 of the cannula 600. This is enhanced by the fact that no portions of the surgical instrument 400 extend radially outward of the links 510–530 and so the surgical instrument can be "pistoned" or moved axially with little restriction even when the movable stem section 420 is bent at 90° or more. These features provide a much larger operating field than is available with a surgical instrument which bends to 90° at only one location along its length.

It should be understood that the present invention is not limited to bending movement of, for example, 90° or more. Thus, the movable stem section of might be independently bendable at, say, 18° at each of ten different locations along the length of the bendable portion, thus providing a total of 180° of bending movement.

FIGS. 20 and 21 illustrate a portion, i.e., the movable stem section 420a, of a surgical instrument 650 which is constructed in accordance with a seventh embodiment of the present invention. Since the embodiment of the invention illustrated in FIGS. 20 and 21 is generally similar to the embodiment of the invention illustrated in FIGS. 11–19, similar reference numerals are used to designate similar components, the suffix letter "a" being associated with the numerals of FIGS. 20 and 21 to avoid confusion. Components of the surgical instrument 650 which are shown incompletely or not at all, such as the rigid stem section and the handle assembly, are the same as the corresponding components in the surgical assembly 400.

In the surgical instrument 650 (FIGS. 20 and 21) a cylindrical metal tube 652 is used in place of the spring 550. The metal tube 652 has a cylindrical inner surface 654 and a cylindrical outer surface 656, each of which extends parallel to the central axis 500a when the surgical instrument 650 is linear. The tube 652 is made from a flexible, resilient metal. The preferred material is TINEL® brand metal, which is a superelastic nickel-titanium alloy available from Raychem Corporation of Menlo Park, Calif. After an apparent plastic deformation to strain the metal more than ten times the elastic limit of stainless steel, a Tinel shape-memory alloy returns to its original shape each time the deforming load is released. No temperature change is required to induce this superelasticity.

Also, the Tinel material does not take a permanent set when bent to a position off the central axis 500a. Like the spring 550, the tube 652 exhibits a self-centering effect and thus tends to attempt to return the movable stem section 420a of the surgical instrument 650 to its linear condition, as illustrated in FIG. 20, after it is bent off the central axis 500a. Thus, like the spring 550, the tube 652 may obviate a return spring such as the return spring 464 (FIG. 11) and/or the lower deflection control wires 474a and 476a. The tube 652, because it is made from metal, also provides a substantial amount of structural support for the movable stem section 420 of the surgical instrument 650.

The embodiment of the invention illustrated in FIGS. 20-21 includes a push rod 454a in place of the pull wire 454 illustrated in FIGS. 10-19. The push rod 454a functions to transmit force from the trigger (not shown) of the surgical instrument 650 to the pituitary rongeur 424a. The trigger of the surgical instrument 650 is modified in a known manner to transmit compressive force over the push rod 454a rather than to apply tensile force to a pull wire such as the pull wire 454.

FIGS. 22 and 23 illustrate a portion, i.e., the movable stem section 420b, of a surgical instrument 670 which is constructed in accordance with an eighth embodiment of the present invention. Components of the surgical instrument 670 which are shown either incompletely or not at all are the same as corresponding components of the surgical instrument 650 (FIGS. 20–21). Since the embodiment of the invention illustrated in FIGS. 22 and 23 is similar to the embodiment of the invention illustrated in FIGS. 20 and 21, similar reference numerals are used to designate similar components, the suffix letter "b" being associated with the numerals of FIGS. 22 and 23 to avoid confusion.

The surgical instrument 670 includes a resilient metal tube 652b which is made from the same material as and which has the same characteristics as the metal tube 652 (FIGS. 20–21). A polymeric sheath 680 overlies the metal tube 652b. The sheath 680 is made from a body of plastic material which exhibits the characteristics of resilience and low bending resistance. The sheath 680 is preferably made from SILASTIC® brand polymer which is available from Dow Corning Corporation of Midland, Michigan. This polymer is comparable in physical character to milled and compounded rubber prior to vulcanization but containing organosilicon polymers.

The sheath 680 has a generally tubular construction and has parallel, axially extending, cylindrical inner and outer surfaces 682 and 684. Four deflection control wires 470b–476b extend axially through deflection control wire passages in the outer surface 684 of the sheath 680. The sheath 680 supports and guides the deflection control wires 470b–476b. The pull wire 454b extends axially through a central passage 554b in the metal tube 652b.

The outer surface 684 of the sheath 680 is circumferentially relieved or indented or grooved at predetermined locations to control the bending characteristics of the movable stem section 420b of the surgical instrument 670. Specifically, a series of circumferential grooves 690–712 is formed in the outer surface 684 of the sheath 680. Each one of the grooves 690–712 extends perpendicular to the axis. The bending resistance of the sheath 680 and, thereby, of the movable stem section 420b of the surgical instrument 670, is controlled by the depth, width, and placement of the grooves 690–712 in the sheath.

For example, a first series or group 690–694 of the grooves 690–712 have an arcuate cross-sectional configuration and have a first depth, i.e. radial extent. The grooves 690–694 are spaced apart by a first distance along the length of the movable stem section 420b of the surgical instrument 670. The first distance is relatively small and, accordingly, the bending resistance of the sheath 680, in this segment (at the location of the grooves 690–694), is relatively low.

In contrast, the remaining grooves 694–706 are spaced apart by a second distance along the length of the movable stem section 420b of the surgical instrument 670. The second distance is substantially greater than the first distance. This tends to increase the bending resistance of the sheath 680 in this segment (at the location of the grooves 694–706), to a level which is relatively high and is greater than the bending resistance of the sheath at the location of the grooves 690–694.

As another example, the grooves 710 and 712 on the movable stem section 420b of the surgical instrument 670 are deeper than the other grooves 690–708. That is, the grooves 710 and 712 have a second depth, i.e., radial extent, which is greater than the first depth of the other grooves 690–708. This tends to decrease the bending resistance of the sheath 680, in this segment (at the location of the grooves 710 and 712), to a level which is less than the bending resistance at other locations.

FIGS. 24 and 25 illustrate a portion of a surgical instrument 750 which is constructed in accordance with a ninth embodiment of the present invention. Components of the surgical instrument 670 which are not shown are the same as corresponding components of the surgical instrument 670 (FIGS. 22 and 23). Since the embodiment of the invention illustrated in FIGS. 24 and 25 is similar to the embodiment of the invention illustrated in FIGS. 22 and 23, similar reference numerals are used to designate similar components, the suffix letter "c" being associated with the numerals of FIGS. 24 and 25 to avoid confusion.

The surgical instrument 750 has a central passage 752 defined by a resilient metal tube 652c which is made from the same material as and which has the same characteristics as the metal tube 652b (FIGS. 22–23). A polymeric member or tube 754 overlies the metal tube 652c. The polymeric tube 754 is made from a body of plastic material which exhibits resilience and low bending resistance. The polymeric tube 754 is preferably made from TEFLON® brand polytetrafluoroethylene which is available from E. I. DuPont de Vemenus and Company.

The polymeric tube 754 has a generally tubular configuration including parallel, axially extending, cylindrical inner and outer surfaces 756 and 758. Four axially extending deflection control wire passages 760, 762, 764 and 766 are formed in the outer surface of the polymeric tube 752. Deflection control wires 470c–476c extend through the deflection control wire passages 760–766 in the polymeric tube 752. A pull wire 454c extends through the central passage 752 in the inner metal tube 652c.

An outer metal tube 770 overlies the outer surface 758 of the polymeric tube 754. The outer metal tube 770 is made from the same material (TINEL®) as the inner metal tube 652c, and has similar characteristics to the inner metal tube 652c. Because of the presence of the two TINEL tubes, the movable stem section 420c of the surgical instrument 750 has a strong self-centering characteristic, yet is light in weight and low in mass.

FIGS. 26 and 27 illustrate a portion, i.e., the movable stem section 420d, of a surgical instrument 800 which is constructed in accordance with a tenth embodiment of the present invention. Since the embodiment of the invention illustrated in FIGS. 26 and 27 is similar to the embodiment of the invention illustrated in FIGS. 20 and 21, similar reference numerals are used to designate similar components, the suffix letter "d" being associated with the numerals of FIGS. 26 and 27 to avoid confusion.

The bendable portion 420d of the surgical instrument 800 includes a polymeric tube 802. The polymeric tube 802 is preferably made from the same material as the polymeric tube 754 (FIGS. 24–25) and exhibits the characteristics of resilience and low bending resistance. The polymeric tube 802 has a generally tubular configuration including parallel, axially extending, cylindrical inner and outer surfaces 804 and 806. A single deflection control wire passage 808 extends axially along the outer surface 806 of the polymeric tube 802. A single deflection control wire 810 extends through the deflection control wire passage 808 in the polymeric tube 802. A pull wire 454d passes through a central passage 812 in the polymeric tube 802. It should understood that in any of the illustrated embodiments of the invention (a) the pull wire 454 could be replaced by a push rod, and (b) either one or multiple (such as four) deflection control wires can be utilized.

The surgical instrument 800 includes a resilient metal outer shaft or outer tube 820 which is made from the TINEL® metal material described above. Specifically, the outer tube 820 is made from a TINEL wire 821 which has a rectangular cross-sectional configuration and which is shaped into a cylindrical helical spring. The outer tube 820 overlies the outer surface 806 of the polymeric tube 802.

The outer tube 820 as formed in the spring configuration illustrated in FIG. 26 includes a series of turns 822–846. The distance between any given pair of turns along the length of the movable stem section 420d of the surgical instrument 800 is predetermined. The bending resistance of the tube 820 and, thereby, of the movable stem section 420d of the surgical instrument, is controlled by the spacing between the adjacent turns 822–846 at any given point along the length of the movable stem section.

For example, the turns 822–826 are spaced apart by a first distance along the length of the movable stem section 420d of the surgical instrument 800. The first distance is relatively small. The bending resistance of the metal tube 820, and thus of the movable stem section 420d, in this segment (at the location of the turns 822–826), is relatively low because the wire 821 is less straight and the turns 822–826 are relatively close together.

In contrast, the turns 830–846 are spaced apart by a second distance along the length of the movable stem section 420d of the surgical instrument 800. The second distance is substantially greater than the first distance and is relatively large. Accordingly, the wire 821 is straighter and the bending resistance of the tube 820 in this segment, (at the location of the turns 830–846), is greater than the bending resistance at the location of the turns 822–826.

Although not illustrated, the bending resistance of the metal tube 820 and, thereby, of the movable stem section 420d of the surgical instrument 800, can also be controlled by varying the width of the metal strip or wire 821 which forms the turns 822–846 at any given point along the length of the movable stem section of the surgical instrument.

FIGS. 28 and 29 illustrate a portion, i.e., a movable stem section 420e, of a surgical instrument 850 which is constructed in accordance with a an eleventh embodiment of the present invention. Since the embodiment of the invention illustrated in FIGS. 28 and 29 is similar to the embodiment of the invention illustrated in FIGS. 26 and 27, similar reference numerals are used to designate similar components, the suffix letter "e" being associated with the numerals of FIGS. 28 and 29 to avoid confusion.

In the surgical instrument 850, the polymeric tube 802e is covered by a resilient metal outer tube or shaft 852 made from TINEL which is selectively slotted or relieved to lower its bending resistance in a predetermined manner. The outer tube 852 has a cylindrical cross-sectional configuration including parallel, axially extending, inner and outer side surfaces 851 and 853.

A first series of slots 852–874 is formed in the upper (as viewed in FIGS. 28 and 29) portion of the outer tube 852. A second series of slots 880–904 is formed in the lower (as viewed in FIGS. 28 and 29) portion of the outer tube 852. The slots in the tube 852 define between them a series of relatively movable link portions of the tube, and the slots act as pivot joints between the link portions. The distance between any given pair of slots is predetermined and may vary between adjacent pairs of slots along the length of the movable stem section 420e to vary the bending resistance of the tube 852 and thus of the movable stem section of the surgical instrument 850.

For example, the slots 868, 870 and 872 are spaced apart by a first distance along the length of the movable stem section 420e of the surgical instrument 850. The first distance is relatively large. This tends to increase the bending resistance of the tube 852, and thus of the movable stem section 420e, at the location of the slots 868, 870 and 872, because the slots are relatively far apart.

In contrast, the slots 858 and 860 are spaced apart by a second distance along the length of the movable stem section 420e of the surgical instrument 850. The second distance is substantially less than the first distance. Accordingly, this tends to decrease the bending resistance of the tube 852, at the location of the slots 858 and 860, to a level which is less than the bending resistance at the location of the slots 868, 870 and 872.

Further, the width of any given slot is predetermined and may vary from slot to slot along the length of the movable stem section 420e to vary the bending resistance of the tube 852 and thus of the movable stem section of the surgical instrument 850. For example, the width of the slots 852, 854 and 856 is relatively great. This tends to lower the bending resistance of the tube 852, and thus of the movable stem section 420e of the surgical instrument 850, at the location of the slots 852, 854 and 856. In contrast, the width of the slots 858–872 is relatively less. This tends to increase the bending resistance of the tube 852, and thus of the movable stem section 420e of the surgical instrument 850, at the location of the slots 858–872.

Devices constructed in accordance with the present invention which are uniform along their length, that is, which have no variation in the features, bend in one manner only when bent in free space (for example, as viewed in FIG. 19). In this case, a cannula or a wall of a body space, for example, is used to restrict and control the movement of the bendable portion of the device. Such devices exhibit uniform bending resistance along the length of the movable stem section, and include the surgical instrument 400 (FIGS. 10–19), the surgical instrument 650 (FIGS. 20–21), and the surgical instrument 750 (FIGS. 24–25).

In contrast, devices constructed in accordance with the present invention which are non-uniform along their length, that is, which have features to selectively vary the bending resistance along their length, can bend at different locations along their length even when bent in free space. In this case, a cannula or a wall of a body space, for example, may not be necessary to restrict and control the movement of the bendable portion of the device. Such devices include the surgical instrument 670 (FIGS. 22–23), the surgical instrument 800 (FIGS. 26–27), and the surgical instrument 850 (FIGS. 28–29).

Figure 30:
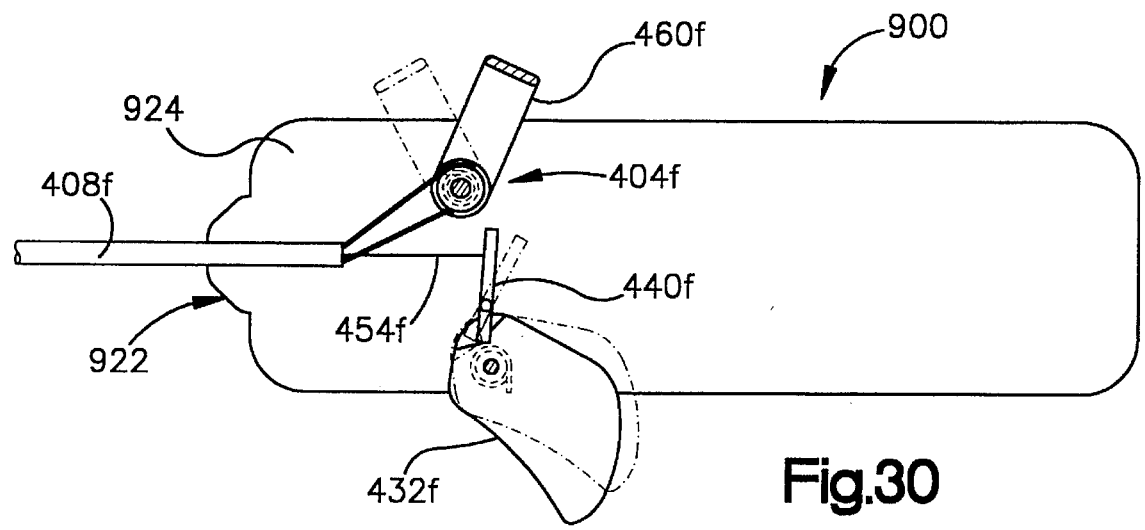
FIG. 30 is a schematic side elevational view, generally similar to FIG. 11, showing a portion of a surgical instrument including a handle assembly which is constructed in accordance with an alternative embodiment of the present invention.

FIG. 30 illustrates a portion of a surgical instrument 920 which is constructed in accordance with a twelfth embodiment of the present invention. Components of the surgical instrument 920 which are not shown are the same as corresponding components of the surgical instrument 400 (FIGS. 10–19). Since the embodiment of the invention illustrated in FIG. 30 is similar to the embodiment of the invention illustrated in FIGS. 10–19, similar reference numerals will be utilized to designate similar components, the suffix letter "f" being associated with the numerals of FIG. 30 to avoid confusion.

The surgical instrument 920 includes a handle 922 having a main body portion 924 which is shaped differently from the handle 402 (FIGS. 10 and 11). Specifically, the main body portion 924 of the handle 922 (FIG. 30) is shaped or configured like the handle or grip of a screwdriver, rather than like the pistol-grip configuration of the handle 402 (FIGS. 10 and 11). The deflection control lever 460f and the trigger 432f are mounted on opposite sides (upper and lower as viewed in FIG. 30) of the main body portion 924 of the handle 922. This alternative handle construction is illustrative of the fact that the present invention is not limited to any one particular handle configuration.

Figure 31:
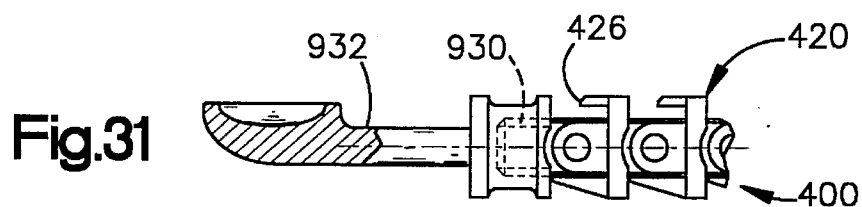
FIG. 31 is a side elevational view, partially in section, showing a removable curet mounted on the distal end of the movable stem section of the surgical instrument of FIG. 10.
Figure 32:
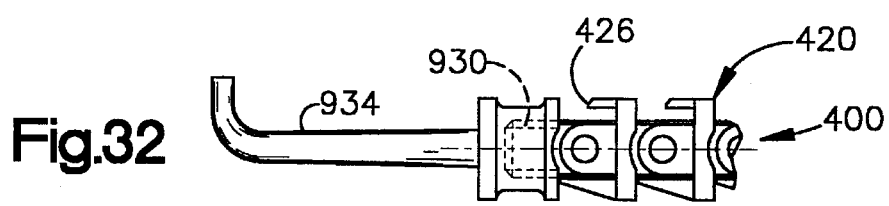
FIG. 32 is a view similar to FIG. 31 showing a removable probe mounted on the surgical instrument in place of the curet.
Figure 33:
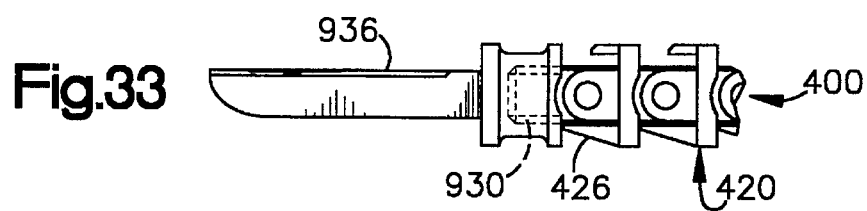
FIG. 33 is a view similar to FIG. 31 showing a removable knife mounted on the end of the surgical instrument.

FIGS. 31–33 are a series of views which illustrate a system for interchangeably mounting a selected one of a plurality of removable tools on the distal end portion 426 of the movable stem section 420 of the surgical instrument 400. It should be understood that the structures shown in FIG. 31–33 are equally usable in association with any others of the surgical instruments shown herein.

In FIG. 31, a platform 930 is mounted on the distal end portion 426 of the movable stem section 420 of the surgical instrument 400. The platform 930 has an externally threaded portion, indicated by the dashed lines, for threadedly receiving a selected one of a plurality of removable tools 932–936. In FIG. 31, for example, a curet 932 is screwed onto the platform 930. In FIG. 32, a probe 934 is screwed onto the platform 930 in place of the curet 932. In FIG. 33, a knife 936 is screwed onto the platform 930. The platform 930 may have an alternative construction, such as a collet or chuck for releasably gripping and for interchangeably receiving the tools 932–936 and/or other tools.

From the above description of the invention, those skilled in the art will perceive improvements, changes and modifications in the invention. Such improvements, changes and modifications within the skill of the art are intended to be covered by the appended claims.

Having described the invention, we claim:

1. A surgical instrument comprising:

a manually engageable handle;

a first stem section having a longitudinal axis and extending from said handle;

tissue engaging means for engaging tissue, said tissue engaging means including at least a first tissue engaging member;

a second stem section connected between said first stem section and said tissue engaging means, said second stem section having at least a portion which is bendable, said second stem section supporting said tissue engaging means for movement between a plurality of orientations relative to said axis and to said first stem section;

means for supporting said first tissue engaging member on said bendable portion of said second stem section; and means for bending said bendable portion of said second stem section to change the orientation of said tissue engaging means relative to said axis and to said first stem section from a first orientation to a second orientation;

said bendable portion of said second stem section comprising means for enabling bending movement of said bendable portion to locate said tissue engaging means at the same angle relative to said longitudinal axis of said first stem section at more than one location along the length of said bendable portion.

2. A surgical instrument as set forth in claim 1 wherein said bendable portion of said second stem section comprises means for enabling bending movement of said bendable portion to locate said tissue engaging means at an angle of 90° relative to said longitudinal axis of said first stem section at more than one location along the length of said bendable portion.

3. A surgical instrument as set forth in claim 1 wherein said bendable portion of said second stem section comprises a plurality of independently movable links and said means for enabling bending movement comprises a plurality of pivot joints, each one of said pivot joints defining a respective pivot axis, each one of said pivot joints interconnecting a pair of adjacent ones of said plurality of links for relative pivotal movement about a respective pivot axis, all of said pivot axes extending generally parallel to each other.

4. A surgical instrument as set forth in claim 3 wherein each one of said links comprises a rigid member having at least one pivot pin which is received in a socket of an adjoining link, said pivot pins and said sockets defining said pivot joints.

5. A surgical instrument as set forth in claim 3 further comprising a tubular stabilizing member extending axially within said links, said means for bending comprising means extending along said tubular stabilizing member and connected with said tissue engaging means for transmitting force to said tissue engaging means to change the orientation of said tissue engaging means relative to said axis and to said first stem section.

6. A surgical instrument as set forth in claim 5 wherein said tubular stabilizing member comprises a coil spring.

7. A surgical instrument as set forth in claim 5 wherein said tubular stabilizing member comprises a metal tube.

8. A surgical instrument as set forth in claim 7 wherein said metal tube is made from a superelastic nickel-titanium alloy.

9. A surgical instrument as set forth in claim 5 wherein said tubular stabilizing member is made from metal and further comprising a cylindrical plastic tube which is coaxially extensive with and disposed radially outwardly of said metal tubular stabilizing member.

10. A surgical instrument as set forth in claim 3 further comprising a tubular plastic stabilizing member extending axially within said links, said means for bending comprising at least one deflection control wire which is disposed radially outward of said tubular plastic member.

11. A surgical instrument as set forth in claim 1 wherein said handle includes a first member which is manually engageable to transmit force to said bendable portion of said second stem section to bend said bendable portion and a second member which is manually engageable to transmit force to said tissue engaging means to engage tissue with said tissue engaging means.

12. A surgical instrument as set forth in claim 11 wherein said handle has a pistol-grip configuration.

13. A surgical instrument as set forth in claim 11 wherein said handle has a screwdriver-grip configuration.

14. A surgical instrument as set forth in claim 1 wherein said tissue engaging means comprises a curet.

15. A surgical instrument as set forth in claim 1 wherein said tissue engaging means comprises a probe.

16. A surgical instrument as set forth in claim 1 wherein said tissue engaging means comprises a knife.

17. A surgical instrument as set forth in claim 1 wherein said tissue engaging means comprises platform means for interchangeably receiving a selected one of a plurality of removable tools such as a curet, a probe, or a knife.

18. A surgical instrument as set forth in claim 1 wherein said tissue engaging means comprises a second tissue engaging member which is pivotally movable relative to said first tissue engaging member to engage tissue between said first and second tissue engaging members when said tissue engaging means is in an orientation between 0° and 180° to said longitudinal axis of said first stem section at any selected location along the length of said bendable portion.

19. A surgical instrument as set forth in claim 18 wherein said tissue engaging means comprises a pituitary rongeur.

20. A surgical instrument as set forth in claim 18 wherein said tissue engaging means comprises a tool selected from the group consisting of scissors, forceps, and basket cutter.

21. A surgical instrument as set forth in claim 1 wherein said means for enabling bending movement comprises means for selectively providing a predetermined first degree of bending resistance of said bendable portion at a first location along the length of said bendable portion and for selectively providing a predetermined second degree of bending resistance of said bendable portion at a second location along the length of said bendable portion, said second degree of bending resistance being greater than said first degree of bending resistance.

22. A surgical instrument as set forth in claim 1 wherein said bendable portion of said second stem section comprises a tubular plastic body portion having surface indentations located at predetermined locations spaced apart along the length of said plastic body portion for decreasing the bending resistance of said plastic body portion at said predetermined locations.

23. A surgical instrument as set forth in claim 22 wherein said tubular plastic body portion has an inner peripheral surface defining an axially extending central passage, said bendable portion of said second stem section further comprising a resilient metal tube longitudinally co-extensive with said plastic body portion and disposed within said central passage in said plastic body portion.

24. A surgical instrument as set forth in claim 23 wherein said metal tube is made from a superelastic nickel-titanium alloy.

25. A surgical instrument as set forth in claim 22 wherein said surface indentations comprise at least a first set of surface indentations having a first configuration for providing a first degree of bending resistance at the location of said first set of surface indentations and a second set of surface indentations having a second configuration different from said first configuration for providing a second degree of bending resistance at the location of said second set of surface indentations, said second degree of bending resistance being greater than said first degree of bending resistance.

26. A surgical instrument as set forth in claim 1 wherein said bendable portion comprises a tubular plastic member having an inner side surface defining an axially extending central passage and having an outer side surface, a first resilient metal tube overlying said outer side surface of said tubular plastic member, and a second resilient metal tube disposed within said central passage in said tubular plastic member.

27. A surgical instrument as set forth in claim 26 wherein said each one of said first and second resilient metal tubes is made from a superelastic nickel-titanium alloy.

28. A surgical instrument as set forth in claim 27 wherein said second resilient metal tube defines a passage extending along said longitudinal central axis of said surgical instrument, said surgical instrument further comprising means extending through said passage in said second resilient metal tube and connected with said tissue engaging means for transmitting force to said tissue engaging means to engage tissue with said tissue engaging means.

29. A surgical instrument as set forth in claim 27 further comprising control wire means extending within said first resilient metal tube and connected with said tissue engaging means for transmitting force to said tissue engaging means to change the orientation of said tissue engaging means relative to said axis and to said first stem section.

30. A surgical instrument as set forth in claim 1 wherein said bendable portion of said second stem section comprises:

a tubular plastic body portion having an outer side surface and an axially extending central passage; and a resilient metal tube overlying said outer side surface of said plastic body portion, said resilient metal tube being configured as a helical coil spring.

31. A surgical instrument as set forth in claim 30 wherein said resilient metal tube is made from a superelastic nickel-titanium alloy.

32. A surgical instrument as set forth in claim 30 wherein said helical coil spring is made from an elongate metal member having a rectangular cross sectional configuration.

33. A surgical instrument as set forth in claim 30 wherein said resilient metal tube comprises means for providing a first degree of bending resistance of said resilient metal tube at a first location along the length of said bendable portion of said second stem section and for providing a second degree of bending resistance of said resilient metal tube at a second location along the length of said bendable portion of said second stem section, said second degree of bending resistance being greater than said first degree of bending resistance.

34. A surgical instrument as set forth in claim 1 wherein said bendable portion of said second stem section comprises a tubular plastic body portion having an outer side surface and a resilient metal tube overlying said outer side surface of said plastic body portion, said means for enabling bending movement comprising a series of slots which are formed in said resilient metal tube and which divide said resilient metal tube member into a series of link portions which are spaced along the length of said bendable portion of said second stem section.

35. A surgical instrument as set forth in claim 34 wherein said series of slots comprises at least a first set of slots having a first configuration for providing a first degree of bending resistance of said resilient metal tube at the location of said first set of slots and a second set of slots having a second configuration different from said first configuration for providing a second degree of bending resistance of said resilient metal tube at the location of said second set of slots, said second degree of bending resistance being greater than said first degree of bending resistance.

36. A surgical instrument as set forth in claim 35 wherein each one of said first set of slots has a first predetermined extent along the length of said bendable portion of said second stem section and each one of said second set of slots has a second predetermined extent along the length of said bendable portion of said second stem section which is less than said first predetermined extent.

37. A surgical instrument as set forth in claim 34 wherein said link portions have predetermined different lengths along the length of said bendable portion of said second stem section to vary the bending resistance of said resilient metal tube.

38. A surgical instrument as set forth in claim 1 further comprising a pull wire extending in a passage through said first stem section and said second stem section, said pull wire transmitting force from said handle to said tissue engaging means to engage tissue with said tissue engaging means.

39. A surgical instrument as set forth in claim 1 further comprising a push rod extending in a passage through said first stem section and said second stem section, said push rod transmitting force from said handle to said tissue engaging means to engage tissue with said tissue engaging means.

40. A surgical instrument comprising:

a manually engageable handle;

a first stem section having a longitudinal axis and extending from said handle;

tissue engaging means for engaging tissue, said tissue engaging means including at least a first tissue engaging member;

a second stem section connected between said first stem section and said tissue engaging means, said second stem section having at least a portion which is bendable, said second stem section supporting said tissue engaging means for movement between a plurality of orientations relative to said axis and to said first stem section;

means for supporting said tissue engaging means on said bendable portion of said second stem section; and means for bending said bendable portion of said second stem section to change the orientation of said tissue engaging means relative to said axis and to said first stem section from a first orientation to a second orientation, said means for bending including a plurality of elongate control members extending axially along said first and second stem sections;

said movable portion of said second stem section comprising:

a resilient inner tubular member defining a central passage in said second stem section through which said elongate actuator member extends, said inner tubular member being made from a superelastic metal;

a flexible outer tubular member coaxial with and disposed radially outward of said inner tubular member; and passage means for defining a plurality of control member passages disposed radially between said inner tubular member and said outer tubular member, said elongate control members extending through said control member passages.

41. A surgical instrument comprising:

a manually engageable handle;

a first stem section having a longitudinal axis and extending from said handle;

tissue engaging means for engaging tissue, said tissue engaging means including at least a first tissue engaging member;

a second stem section connected between said first stem section and said tissue engaging means, said second stem section having at least a portion which is bendable, said second stem section supporting said tissue engaging means for movement between a plurality of orientations relative to said axis and to said first stem section;

means for supporting said first tissue engaging member on said bendable portion of said second stem section; and means for bending said bendable portion of said second stem section to change the orientation of said tissue engaging means relative to said axis and to said first stem section from a first orientation to a second orientation;

said movable portion of said second stem section comprising a plurality of independently movable link portions and a plurality of pivot joints, each pivot joint defining a respective pivot axis, each pivot joint interconnecting a pair of adjacent ones of said plurality of link portions for relative pivotal movement about its respective pivot axis, all of said pivot axes extending generally parallel to each other.

42. A surgical instrument comprising:

a manually engageable handle;

a first stem section having a longitudinal axis and extending from said handle;

tissue engaging means for engaging tissue, said tissue engaging means including at least a first tissue engaging member;

a second stem section connected between said first stem section and said tissue engaging means, said second stem section having at least a portion which is bendable, said second stem section supporting said tissue engaging means for movement between a plurality of orientations relative to said axis and to said first stem section;

means for supporting said first tissue engaging member on said bendable portion of said second stem section; and means for bending said bendable portion of said second stem section to move said tissue engaging means through an arcuate path between a plurality of orientations relative to said axis and to said first stem section;

said bendable portion of said second stem section comprising means for enabling bending movement of said bendable portion of said second stem section to move said tissue engaging means through a plurality of arcuate paths which are of different lengths and which are spaced apart from each other along said longitudinal axis.

43. A surgical instrument as set forth in claim 42 wherein said means for enabling bending movement comprises a plurality of joints which are spaced along the length of said bendable portion and at which said bendable portion is bendable to locate said tissue engaging means at the same angle relative to said longitudinal axis of said first stem section, at each one of said joints, each joint being bendable independently of the other said joint.

44. A surgical instrument as set forth in claim 43 wherein said joints comprise pivot joints interconnecting a plurality of links which form said bendable portion of said second stem section, each one of said pivot joints being bendable independently of the other ones of said pivot joints.

45. A surgical instrument as set forth in claim 43 wherein said joints comprise slots formed in a tubular outer member which is axially coextensive with said bendable portion of said second stem section.

46. A surgical instrument as set forth in claim 43 wherein said joints comprise recessed portions formed in a polymeric member which is axially coextensive with said bendable portion of said second stem section.

47. A surgical instrument as set forth in claim 42 wherein said means for enabling bending movement comprises means for enabling movement of said bendable portion of said second stem section, at more than one location along the length of said bendable portion, into a condition in which said bendable portion has a first segment extending parallel to said axis and a second segment which extends at an angle relative to said axis and to said first stem section.

* * * * *